(12) United States Patent
Porambo et al.

(10) Patent No.: US 11,491,216 B2
(45) Date of Patent: Nov. 8, 2022

(54) PNEUMOCOCCAL POLYSACCHARIDES AND THEIR USE IN IMMUNOGENIC POLYSACCHARIDE-CARRIER PROTEIN CONJUGATES

(71) Applicants: Merck Sharp & Dohme Corp., Rahway, NJ (US); Richard J. Porambo, Norristown, PA (US); Chitrananda Abeygunawardana, Ambler, PA (US); Luwy Kavuka Musey, Blue Bell, PA (US); Michael J. Kosinski, Souderton, PA (US); Yadong Adam Cui, Norristown, PA (US); Julie Marie Skinner, Phoenixville, PA (US)

(72) Inventors: Richard J. Porambo, Norristown, PA (US); Chitrananda Abeygunawardana, Ambler, PA (US); Luwy Kavuka Musey, Blue Bell, PA (US); Michael J. Kosinski, Souderton, PA (US); Yadong Adam Cui, Norristown, PA (US); Julie Marie Skinner, Phoenixville, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 16/645,048

(22) PCT Filed: Sep. 4, 2018

(86) PCT No.: PCT/US2018/049306
§ 371 (c)(1),
(2) Date: Mar. 6, 2020

(87) PCT Pub. No.: WO2019/050814
PCT Pub. Date: Mar. 14, 2019

(65) Prior Publication Data
US 2020/0330578 A1 Oct. 22, 2020

Related U.S. Application Data

(60) Provisional application No. 62/555,455, filed on Sep. 7, 2017.

(51) Int. Cl.
*A61K 39/09* (2006.01)
*A61K 39/39* (2006.01)
*A61K 47/42* (2017.01)

(52) U.S. Cl.
CPC ............ *A61K 39/092* (2013.01); *A61K 39/39* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 5,623,057 A | 4/1997 | Marburg et al. | |
| 5,847,112 A | 12/1998 | Kniskern et al. | |
| 8,192,746 B2 | 6/2012 | Caulfield et al. | |
| 9,101,582 B2 * | 8/2015 | Ades | A61K 31/00 |
| 9,981,045 B2 * | 5/2018 | Prasad | A61K 47/646 |
| 10,124,050 B2 * | 11/2018 | Watson | C08B 37/006 |
| 10,307,474 B2 * | 6/2019 | Faridmoayer | C12Y 204/99 |
| 10,668,164 B2 * | 6/2020 | Gu | A61K 39/092 |
| 10,716,848 B2 * | 7/2020 | Hausdorff | A61P 27/16 |
| 10,729,780 B2 * | 8/2020 | Dhere | A61K 47/22 |
| 10,780,160 B2 * | 9/2020 | Hausdorff | A61P 11/00 |
| 11,090,374 B2 * | 8/2021 | He | A61K 39/116 |
| 11,116,828 B2 * | 9/2021 | Smith | A61K 47/10 |
| 2010/0092519 A1 * | 4/2010 | Gorringe | A61P 35/04 424/250.1 |
| 2013/0273098 A1 * | 10/2013 | Blue | A61K 47/646 424/197.11 |
| 2013/0315958 A1 | 11/2013 | Nahm et al. | |
| 2015/0132339 A1 * | 5/2015 | Bufali | A61K 31/4745 424/197.11 |
| 2015/0202309 A1 | 7/2015 | Emini et al. | |
| 2017/0021006 A1 * | 1/2017 | Watson | C08H 1/00 |
| 2017/0232093 A1 * | 8/2017 | Faridmoayer | A61K 39/092 424/197.11 |
| 2018/0099039 A1 | 4/2018 | Emini et al. | |

(Continued)

FOREIGN PATENT DOCUMENTS

| | | | | |
|---|---|---|---|---|
| EP | 0497524 A2 | 8/1992 | | |
| EP | 3655030 A1 * | 5/2020 | ........... | C08B 37/006 |

(Continued)

OTHER PUBLICATIONS

Balsells et al, PLoS ONE 2017, 12/5:e0177113. 20 pages, published: May 9, 2017 (Year: 2017).*
Caro-Aguilar et al., Vaccine 35(2017) 865-872. available online: Jan. 10, 2017 (Year: 2017).*
Ousmane etal, PLoS ONE, 2017, 12/1:e0169547. 12 pages. published: Jan. 19, 2017 (Year: 2017).*
Slotved et al, Vaccine 34 (2016) 769-774. available online: Jan. 6, 2016 (Year: 2016).*
Johannis P. Kamerling, Pneumococcal polysaccharides: a chemical view, *Streptococcus pneumoniae* molecular biology & mechanisms of disease, 2000, 81-114, –, In Tomasz A (ed), Mary Ann Liebert, Inc.

(Continued)

*Primary Examiner* — Nita M. Minnifield
(74) *Attorney, Agent, or Firm* — Steven C. Pageau; Anna L. Cocuzzo

(57) ABSTRACT

The present invention provides capsular polysaccharides from *Streptococcus pneumoniae* serotypes identified using NMR. The present invention further provides polysaccharide-protein conjugates in which capsular polysaccharides from one or more of these serotypes are conjugated to a carrier protein such as CRM197. Polysaccharide-protein conjugates from one or more of these serotypes may be included in multivalent pneumococcal conjugate vaccines having polysaccharides from multiple additional *Streptococcus pneumoniae* serotypes.

30 Claims, 20 Drawing Sheets

(56) References Cited

U.S. PATENT DOCUMENTS

| | | | |
|---|---|---|---|
| 2019/0119313 A1* | 4/2019 | Seeberger | A61P 31/04 |
| 2019/0192648 A1* | 6/2019 | Smith | A61K 47/22 |
| 2019/0248841 A1* | 8/2019 | Faridmoayer | A61K 39/092 |
| 2020/0054733 A1* | 2/2020 | He | A61K 47/646 |
| 2020/0061179 A1* | 2/2020 | MacNair | A61K 39/092 |
| 2020/0179505 A1* | 6/2020 | Faridmoayer | C12P 19/04 |
| 2020/0188502 A1* | 6/2020 | Faridmoayer | A61P 31/04 |
| 2020/0190549 A1* | 6/2020 | Dhere | A61K 39/095 |
| 2020/0197503 A1* | 6/2020 | Abeygunawardana | A61P 31/04 |
| 2020/0276316 A1* | 9/2020 | McHugh | A61K 47/549 |
| 2020/0282040 A1* | 9/2020 | Porambo | A61P 37/04 |
| 2020/0282070 A1* | 9/2020 | Porambo | A61P 31/04 |
| 2020/0330578 A1* | 10/2020 | Porambo | C08H 1/00 |
| 2021/0038723 A1* | 2/2021 | Porambo | A61P 31/04 |
| 2021/0177957 A1* | 6/2021 | Smith | A61K 39/385 |
| 2021/0221461 A1* | 7/2021 | Nelson | B62J 45/412 |
| 2021/0236646 A1* | 8/2021 | Ahl | A61K 47/61 |
| 2022/0040283 A1* | 2/2022 | Kapre | A61P 31/04 |

FOREIGN PATENT DOCUMENTS

| | | | | |
|---|---|---|---|---|
| EP | 3678655 A1 * | 7/2020 | | A61K 47/42 |
| RU | 2012151376 A | 7/2014 | | |
| RU | 2015103017 A | 10/2016 | | |
| WO | WO-2011100151 A1 * | 8/2011 | | A61P 31/04 |
| WO | 2011151760 A2 | 12/2011 | | |
| WO | WO-2012078482 A1 * | 6/2012 | | A61K 47/646 |
| WO | WO-2013131983 A1 * | 9/2013 | | A61P 11/00 |
| WO | 2014027302 A1 | 2/2014 | | |
| WO | 2017173415 A2 | 10/2017 | | |
| WO | WO-2017178664 A1 * | 10/2017 | | C07H 3/06 |
| WO | WO-2017216286 A1 * | 12/2017 | | C07K 14/3156 |
| WO | 2018156465 A1 | 8/2018 | | |
| WO | WO2018144438 A1 | 8/2018 | | |
| WO | WO2018144439 A1 | 8/2018 | | |
| WO | WO2018156467 A1 | 8/2018 | | |
| WO | WO2018156468 A1 | 8/2018 | | |
| WO | WO2018156491 A1 | 8/2018 | | |
| WO | WO-2019016187 A1 * | 1/2019 | | A61K 39/092 |
| WO | WO-2019016188 A1 * | 1/2019 | | A61P 31/04 |
| WO | WO2019036313 A1 | 2/2019 | | |
| WO | WO2019050813 A1 | 3/2019 | | |
| WO | WO-2019050813 A1 * | 3/2019 | | A61K 47/646 |
| WO | WO2019050814 A1 | 3/2019 | | |
| WO | WO-2019050814 A1 * | 3/2019 | | A61K 39/092 |
| WO | WO2019050816 A1 | 3/2019 | | |
| WO | WO2019050818 | 3/2019 | | |
| WO | WO2019050815 A1 | 4/2019 | | |
| WO | WO2019083865 A1 | 5/2019 | | |
| WO | WO-2019212842 A1 * | 11/2019 | | A61K 39/092 |
| WO | WO-2021010798 A1 * | 1/2021 | | A61K 39/39 |

OTHER PUBLICATIONS

K. Aaron Geno, Pneumococcal Capsules and Their Types: Past, Present, and Future, Clinical Microbiology Reviews, 2015, 871-899, 28.

Ravenscroft, Neil et al., Genetic and structural elucidation of capsular polysaccharides from *Streptococcus pneumoniae* serotype 23A and 23B, and comparison to serotype 23F, Carbohydrate Research, 2017, 19-29, 450.

7f Devi: Purified Pneumococcal Capsular Polysaccharides for in vitro diagnosticUse, Dec. 1, 2016 (Dec. 1, 2016), XP055512967, Retrieved from the Internet: URL:https://www.ssidiagnostica.dk/upload/images/webshop/products/44/downloads/insert-purified-pneumococcal-capsular-polysaccharides-75157.pdf [retrieved on Oct. 5, 2018](1 page).

Devine, V. et al., The rise and fall of pneumococcal serotypes carried in the PCV era, Vaccine, 2017, 1293-1298, 35(9).

* cited by examiner

PNEUMOCOCCAL POLYSACCHARIDES AND THEIR USE IN IMMUNOGENIC POLYSACCHARIDE-CARRIER PROTEIN CONJUGATES

FIELD OF INVENTION

The present invention provides purified capsular polysaccharides from *Streptococcus pneumoniae* serotypes 23A and 23B, and polysaccharide-protein conjugates having polysaccharides from one or more of these serotypes. Polysaccharide-protein conjugates from one of more of these serotypes may be included in multivalent pneumococcal conjugate vaccines.

BACKGROUND OF THE INVENTION

*Streptococcus pneumoniae*, one example of an encapsulated bacterium, is a significant cause of serious disease world-wide. In 1997, the Centers for Disease Control and Prevention (CDC) estimated there were 3,000 cases of pneumococcal meningitis, 50,000 cases of pneumococcal bacteremia, 7,000,000 cases of pneumococcal otitis media and 500,000 cases of pneumococcal pneumonia annually in the United States. See Centers for Disease Control and Prevention, MMWR Morb Mortal Wkly Rep 1997, 46(RR-8):1-13. Furthermore, the complications of these diseases can be significant with some studies reporting up to 8% mortality and 25% neurologic sequelae with pneumococcal meningitis. See Arditi et al., 1998, Pediatrics 102:1087-97.

The multivalent pneumococcal polysaccharide vaccines that have been licensed for many years have proved invaluable in preventing pneumococcal disease in adults, particularly, the elderly and those at high-risk. However, infants and young children respond poorly to unconjugated pneumococcal polysaccharides. Bacterial polysaccharides are T-cell-independent immunogens, eliciting weak or no response in infants. Chemical conjugation of a bacterial polysaccharide immunogen to a carrier protein converts the immune response to a T-cell-dependent one in infants. Diphtheria toxoid (DTx, a chemically detoxified version of DT) and CRM197 have been described as carrier proteins for bacterial polysaccharide immunogens due to the presence of T-cell-stimulating epitopes in their amino acid sequences.

The pneumococcal conjugate vaccine, Prevnar®, containing the 7 most frequently isolated serotypes (4, 6B, 9V, 14, 18C, 19F and 23F) causing invasive pneumococcal disease in young children and infants at the time, was first licensed in the United States in February 2000. Following universal use of Prevnar® in the United States, there has been a significant reduction in invasive pneumococcal disease in children due to the serotypes present in Prevnar®. See Centers for Disease Control and Prevention, MMWR Morb Mortal Wkly Rep 2005, 54(36):893-7. However, there are limitations in serotype coverage with Prevnar® in certain regions of the world and some evidence of certain emerging serotypes in the United States (for example, 19A and others). See O'Brien et al., 2004, Am J Epidemiol 159:634-44; Whitney et al., 2003, N Engl J Med 348:1737-46; Kyaw et al., 2006, N Engl J Med 354:1455-63; Hicks et al., 2007, J Infect Dis 196:1346-54; Traore et al., 2009, Clin Infect Dis 48:S181-S189.

Prevnar 13® is a 13-valent pneumococcal polysaccharide-protein conjugate vaccine including serotypes 1, 3, 4, 5, 6A, 6B, 7F, 9V, 14, 18C, 19A, 19F and 23F. See, e.g., U.S. Patent Application Publication No. US 2006/0228380 A1, Prymula et al., 2006, Lancet 367:740-48 and Kieninger et al., Safety and Immunologic Non-inferiority of 13-valent Pneumococcal Conjugate Vaccine Compared to 7-valent Pneumococcal Conjugate Vaccine Given as a 4-Dose Series in Healthy Infants and Toddlers, presented at the 48$^{th}$ Annual ICAAC/ISDA 46$^{th}$ Annual Meeting, Washington D.C., Oct. 25-28, 2008. See, also, Dagan et al., 1998, Infect Immun. 66: 2093-2098 and Fattom, 1999, Vaccine 17:126.

*S. pneumoniae* has been categorized into more than ninety serotypes based on the structure of the capsular polysaccharide. A list of known pneumococcal capsular polysaccharide structures is provided in Geno, 2015, Clinical Microbiology Reviews 28:871-899. Serotype 23A was described in Italian Patent No. IT 1418572 B1 but no structure was provided.

The current multivalent pneumococcal conjugate vaccines have been effective in reducing the incidence of pneumococcal disease associated with those serotypes present in the vaccines, e.g., 23F. However, the prevalence of the pneumococci expressing serotypes not present in the vaccine has been increasing. Moreover, pneumococcal conjugate vaccines which include 23F do not afford cross protection to serotypes 23A and 23B. Accordingly, there is a need to identify and characterize emerging pneumococcal serotypes for inclusion in future vaccines.

SUMMARY OF THE INVENTION

The present invention provides purified capsular polysaccharides from *Streptococcus pneumoniae* serotypes 23A and 23B, and polysaccharide protein conjugates having these serotypes. The present invention is based, in part, on the structural identification of capsular polysaccharides from these serotypes.

Accordingly, in one embodiment, the present invention provides a polysaccharide with one of the following repeating units:

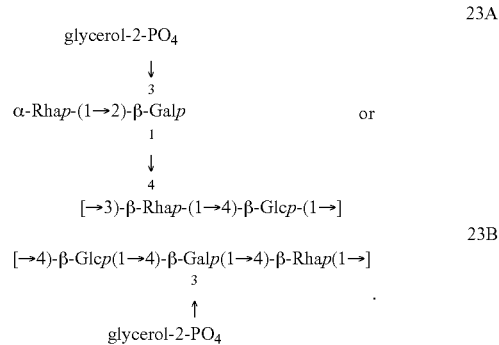

A polysaccharide from *Streptococcus pneumoniae* serotype 23A can be represented by

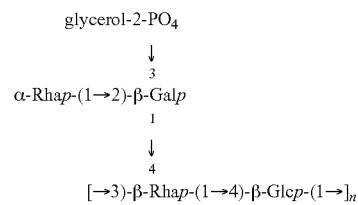

where n represents the number of repeating units.

A polysaccharide from *Streptococcus pneumoniae* serotype 23B can be represented by

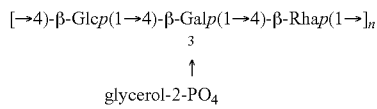
glycerol-2-PO$_4$ where n represents the number of repeating units.

In certain embodiments, the polysaccharide has between 10 and 5,000 repeating units. In certain aspects, the polysaccharide has between 50 and 3,000, 100 and 2,500, or 100 to 2,000 repeating units.

In certain embodiments, the polysaccharide has a molecular weight from 50 kDa to 4,000 kDa. In certain aspects, the polysaccharide has a molecular weight from 80 kDa to 2,000 kDa, or 100 kDa to 1,500 kDa.

The present invention further provides activated polysaccharides produced from any of the above embodiments wherein the polysaccharide is activated with a chemical reagent to produce reactive groups for conjugation to a linker or carrier protein. In certain embodiments, the activation of *S. pneumoniae* serotype polysaccharide 23A occurs on the α-Rhap or β-Glcp. In certain embodiments, the activation of *S. pneumoniae* serotype polysaccharide 23B occurs on the β-Glcp or β-Rhap. In one aspect of this embodiment, activation of *S. pneumoniae* serotype polysaccharide 23B occurs at greater than 90%, 95%, or 99% on the β-Rhap. In certain embodiments, the polysaccharide is activated with periodate. In certain aspects of this embodiment, the activation of the serotype 23A polysaccharide occurs on the $2^{nd}$ or $3^{rd}$ carbon position of α-Rhap or β-Glcp or the activation of the serotype 23B polysaccharide occurs on the $2^{nd}$ or $3^{rd}$ carbon position of β-Glcp or β-Rhap. In one sub-aspect of this aspect, perodiate activation of the serotype 23B polysaccharide occurs at greater than 90%, 95%, or 99% on the β-Rhap.

The present invention further provides polysaccharide-protein conjugates in which polysaccharides or activated polysaccharides as provided for above are conjugated to a carrier protein. In certain aspects, the carrier protein is selected from CRM197, diphtheria toxin fragment B (DTFB), DTFB C8, Diphtheria toxoid (DT), tetanus toxoid (TT), fragment C of TT, pertussis toxoid, cholera toxoid, *E. coli* LT, *E. coli* ST, and exotoxin A from *Pseudomonas aeruginosa*. In one specific aspect, the carrier protein is CRM197.

In certain aspects, the polysaccharide-protein conjugates are prepared using reductive amination chemistry under aqueous conditions or in an aprotic solvent such as dimethyl sulfoxide (DMSO). In a specific aspect, the polysaccharide-protein conjugates are prepared using reductive amination chemistry in DMSO.

In one embodiment, the present invention provides a multivalent immunogenic composition comprising unconjugated polysaccharides or polysaccharide-protein conjugates from one or more of *Streptococcus pneumoniae* serotypes 23A and 23B, and unconjugated polysaccharides or polysaccharide-protein conjugates from one or more of *Streptococcus pneumoniae* serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18B, 18C, 19A, 19F, 20, 21, 22A, 22F, 23F, 24F, 27, 28A, 31, 33F, 34, 35A, 35B, 35F, and 38. In one subembodiment, a multivalent immunogenic composition comprises unconjugated polysaccharides or polysaccharide-carrier protein conjugates but not both. In one subembodiment, a multivalent immunogenic composition comprises a mixture of unconjugated polysaccharides or polysaccharide-carrier protein conjugates. In certain subembodiments, a multivalent immunogenic composition of the invention has up to 4, 5, 6, 7, 8, 9, 10, 11, 12, 13, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, or 90 serotypes.

DETAILED DESCRIPTION OF THE INVENTION

Figure 1A:
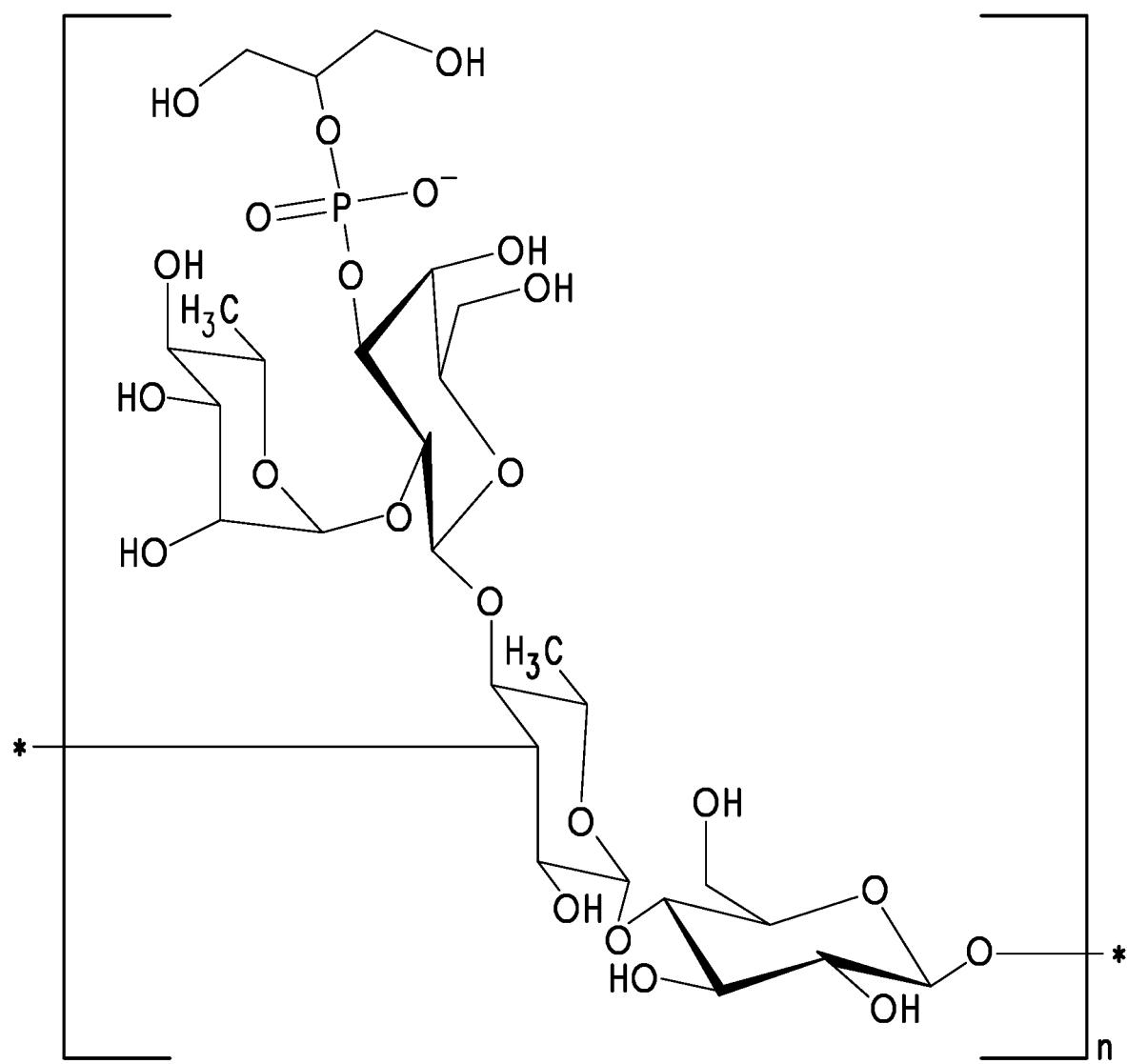
FIGS. 1A-B depicts graphical representations of the repeating unit structure of *S. pneumoniae* serotype 23A (A) and 23B (B) polysaccharides. The activation sites available for periodate are shown with arrows. For an activated polysaccharide, not all of the repeating unit's activation sites are activated. This reflects the possible activation of the serotype 23B polysaccharide on the 2nd or 3rd carbon position of β-Rhap.

The present invention is based, in part, on the identification of novel pneumococcal polysaccharide structures by NMR technology. It is believed that the structures provided herein are the first identification or the first correct identification of these *S. pneumoniae* serotypes 23A and 23B.

The *S. pneumoniae* serotypes 23A and 23B polysaccharides were produced from their respective strains and purified. The produced (and purified) polysaccharides were used to generate individual Ps-CRM197 conjugates. *S. pneumoniae* serotypes 23A and 23B have a unique polysaccharide structure, which results in a conjugate production process. The resulting conjugates were demonstrated to be immunogenic in animal studies.

As used herein, the term "polysaccharide" (Ps) is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate", a "derivatized or activated polysaccharide or oligosaccharide", and the like. Unless otherwise specified, the polysaccharide nomenclature used herein follows the IUB-IUPAC Joint Commission on Biochemical Nomenclature (JCBM) Recommendations 1980. See JCBN, 1982, J. Biol. Chem. 257:3352-3354.

As used herein, "immunogenic composition" refers to a composition containing an antigen, such as a bacterial capsular polysaccharide or a polysaccharide-protein conjugate, that has the ability to elicit an immune response in a host such as a mammal, either humorally or cellularly mediated, or both. The immunogenic composition may serve to sensitize the host by the presentation of the antigen in association with MHC molecules at a cell surface. In addition, antigen-specific T-cells or antibodies can be generated to allow for the future protection of an immunized host. Immunogenic compositions thus can protect the host from infection by the bacteria, reduced severity, or may protect the host from death due to the bacterial infection. Immunogenic compositions may also be used to generate polyclonal or monoclonal antibodies, which may be used to confer passive immunity to a subject. Immunogenic compositions may also be used to generate antibodies that are functional as measured by the killing of bacteria in either an animal efficacy model or via an opsonophagocytic killing assay.

As used herein, the term "isolated" in connection with a polysaccharide refers to isolation of *S. pneumoniae* serotype specific capsular polysaccharide from purified polysaccharide using purification techniques known in the art, including the use of centrifugation, depth filtration, precipitation, ultrafiltration, treatment with activate carbon, diafiltration and/or column chromatography. Generally an isolated polysaccharide refers to partial removal of proteins, nucleic acids and non-specific endogenous polysaccharide (C-polysaccharide). The isolated polysaccharide contains less than 10%, 8%, 6%, 4%, or 2% protein impurities and/or nucleic acids. The isolated polysaccharide contains less than 20% of C-polysaccharide with respect to type specific polysaccharides.

As used herein, the term "purified" in connection with a bacterial capsular polysaccharide refers to the purification of the polysaccharide from cell lysate through means such as centrifugation, precipitation, and ultra-filtration. Generally, a purified polysaccharide refers to removal of cell debris and DNA.

As used herein, the term "Mw" refers to the weight averaged molecular weight and is typically expressed in Da or kDa. Mw takes into account that a bigger molecule contains more of the total mass of a polymer sample than the smaller molecules do. Mw can be determined by techniques such as static light scattering, small angle neutron scattering, X-ray scattering, and sedimentation velocity.

As used herein, the term "Mn" refers to a number average molecular weight and is typically expressed in Da or kDa. Mn is calculated by taking the total weight of a sample divided by the number of molecules in the sample and can be determined by techniques such as gel permeation chromatography, viscometry via the (Mark-Houwink equation), colligative methods such as vapor pressure osmometry, end-group determination or proton NMR. Mw/Mn reflects polydispersity.

As used herein, the term "molar ratio" is a fraction typically expressed as a decimal to the tenths or hundredths place. For example, a molar ratio of from 0 or 0.1 to 1.0 expressed in tenths will include any of 0.1, 0.2, 0.3, 0.4, 0.5, 0.6, 0.7, 0.8, 0.9 or 1.0.

As used herein, the abbreviation "PnPs" refers to pneumococcal polysaccharide.

As used herein, the term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture of the invention refers to a mixture having those particular *S. pneumoniae* polysaccharide protein conjugates and no other *S. pneumoniae* polysaccharide protein conjugates from a different serotype.

As used herein, the phrase "activation site" on a sugar means that the site can be chemically modified to form a reactive group. Activation site takes into account the preferred tendency of an activation agent to react at a specific site.

As used herein, the phrase "activated polysaccharide" refers to a polysaccharide that has been chemically modified to form reactive groups in a polysaccharide chain. An activated polysaccharide does not necessarily mean that all the available activation sites have been chemically modified.

As used herein, the phrase "extent of activation" on a polysaccharide chain refers to the overall ratio between the number of activated chemical group to the number of repeat units on the polysaccharide chain.

Unless otherwise specified, all ranges provided herein are inclusive of the recited lower and upper limits.

Two additional members of *S. pneumoniae* serogroup 23, for which no structure or composition information has been available, have been identified. The serotype 23B polysaccharide has the same backbone as the serotype 23F polysaccharide, but is missing the pendant α-Rhap. In comparison to the serotype 23F polysaccharide, the serotype 23A polysaccharide possesses a shorter backbone and a longer side chain.

The identification of the structure for these serotypes may allow their incorporation into pneumococcal vaccines, either unconjugated or as a polysaccharide-protein conjugate. Conjugate vaccines comprising streptococcal and pneumococcal Ps are well-known in the art. See e.g., U.S. Pat. Nos. 6,248,570; 5,866,135; and 5,773,007.

Capsular Polysaccharides

Capsular polysaccharides from *Streptococcus pneumoniae* from the serotype(s) of the invention can be prepared by standard techniques known to those skilled in the art. For example, polysaccharides can be isolated from bacteria and may be sized to some degree by known methods (see, e.g., European Patent Nos. EP497524 and EP497525); and preferably by microfluidisation accomplished using a homogenizer or by chemical hydrolysis. In one embodiment, *S. pneumoniae* strains corresponding to each polysaccharide serotype are grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112. Polysaccharides can be sized in order to reduce viscosity and/or to improve filterability of subsequent conjugated products. Chemical hydrolysis may be conducted using acetic acid. Mechanical sizing may be conducted using High Pressure Homogenization Shearing.

In some embodiments, the purified polysaccharides before conjugation have a molecular weight of between 5 kDa and 4,000 kDa. Molecular weight can be calculated by size exclusion chromatography (SEC) combined with multiangle light scattering detector (MALS) and refractive index detector (RI). In other such embodiments, the polysaccharide has an average molecular weight of between 10 kDa and 4,000 kDa; between 50 kDa and 4,000 kDa; between 50 kDa and 3,000 kDa; between 50 kDa and 2,000 kDa; between 50 kDa and 1,500 kDa; between 50 kDa and 1,000 kDa; between 50 kDa and 750 kDa; between 50 kDa and 500 kDa; between 80 kDa and 2000 kDa; between 100 kDa and 4,000 kDa; between 100 kDa and 3,000 kDa; 100 kDa and 2,000 kDa; between 100 kDa and 1,500 kDa; between 100 kDa and 1,000 kDa; between 100 kDa and 750 kDa; between 100 kDa and 500 kDa; between 100 and 400 kDa; between 200 kDa and 4,000 kDa; between 200 kDa and 3,000 kDa; between 200 kDa and 2,000 kDa; between 200 kDa and 1,500 kDa; between 200 kDa and 1,000 kDa; or between 200 kDa and 500 kDa. In certain embodiments, the polysaccharide from serotype 23A has an average molecular weight of between 75 kDa and 200 kDa. In certain embodiments, the polysaccharide from serotype 23B has an average molecular weight of between 150 kDa and 250 kDa.

In certain embodiments, the *S. pneumoniae* serotypes 23A or 23B polysaccharide has between 10 and 5,000 repeating units. In certain aspects, the polysaccharide has between 50 and 3,000, 100 to 2,500, or 100 to 2,000. In certain embodiments, the polysaccharide from serotype 23A has between 97 and 260 repeating units. In certain embodiments, the polysaccharide from *S. pneumoniae* serotype 23B has between 195 and 324 repeating units.

Carrier Protein

Polysaccharides from one or more of the serotypes can be conjugated to a carrier protein ("Pr") to improve immunogenicity in children, the elderly and/or immunocompromised subjects. Where more than one serotype is used in a multivalent composition, the serotypes may be prepared with the same carrier protein or different carrier proteins. Each capsular polysaccharide of the same serotype is typically conjugated to the same carrier protein.

In a particular embodiment of the present invention, CRM197 is used as a carrier protein. CRM197 is a non-toxic variant of diphtheria toxin (DT). The CRM197 carrier protein is a mutant form of DT that is rendered non-toxic by a single amino acid substitution in Fragment A at residue 52. In one embodiment, the CRM197 carrier protein is isolated from cultures of *Corynebacterium diphtheria* strain C7 (β197) grown in casamino acids and yeast extract-based medium. In another embodiment, CRM197 is prepared recombinantly in accordance with the methods described in U.S. Pat. No. 5,614,382. Typically, CRM197 is purified through a combination of ultra-filtration, ammonium sulfate precipitation, and ion-exchange chromatography. In some embodiments, CRM197 is prepared in *Pseudomonas fluorescens* using Pfenex Expression Technology™ (Pfenex Inc., San Diego, Calif.).

Other suitable carrier proteins include additional inactivated bacterial toxins such as DT, Diphtheria toxoid fragment B (DTFB), TT (tetanus toxid) or fragment C of TT, pertussis toxoid, cholera toxoid (e.g., as described in International Patent Application Publication No. WO 2004/083251), *E. coli* LT (heat-labile enterotoxin), *E. coli* ST (heat-stable enterotoxin), and exotoxin A from *Pseudomonas aeruginosa*. Bacterial outer membrane proteins such as outer membrane complex c (OMPC), porins, transferrin binding proteins, pneumococcal surface protein A (PspA; See International Application Patent Publication No. WO 02/091998), pneumococcal adhesin protein (PsaA), C5a peptidase from Group A or Group B *streptococcus*, or *Haemophilus influenzae* protein D, pneumococcal pneumolysin (Kuo et al., 1995, Infect Immun 63; 2706-13) including ply detoxified in some fashion for example dPLY-GMBS (See International Patent Application Publication No. WO 04/081515) or dPLY-formol, PhtX, including PhtA, PhtB, PhtD, PhtE and fusions of Pht proteins for example PhtDE fusions, PhtBE fusions (See International Patent Application Publication Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., European Patent No. EP 0 594 610 B), or immunologically functional equivalents thereof, synthetic peptides (See European Patent Nos. EP0378881 and EP0427347), heat shock proteins (See International Patent Application Publication Nos. WO 93/17712 and WO 94/03208), pertussis proteins (See International Patent Application Publication No. WO 98/58668 and European Patent No. EP0471177), cytokines, lymphokines, growth factors or hormones (See International Patent Application Publication No. WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See International Patent Application Publication No. WO 01/72337), toxin A or B of *C. difficile* (See International Patent Publication No. WO 00/61761), and flagellin (See Ben-Yedidia et al., 1998, Immunol Lett 64:9) can also be used as carrier proteins.

Other DT mutants can also be used as the carrier protein, such as CRM176, CRM228, CRM45 (Uchida et al., 1973, J Biol Chem 218:3838-3844); CRM9, CRM45, CRM102, CRM103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragment disclosed in U.S. Pat. No. 5,843,711.

Where multivalent vaccines are used, a second carrier protein can be used for one or more of the antigens. The second carrier protein is preferably a protein that is non-toxic and non-reactogenic and obtainable in sufficient amount and purity. The second carrier protein is also conjugated or joined with an antigen, e.g., a *S. pneumoniae* polysaccharide to enhance immunogenicity of the antigen. Carrier proteins should be amenable to standard conjugation procedures. In one embodiment, each capsular polysaccharide not conjugated to the first carrier protein is conjugated to the same second carrier protein (e.g., each capsular polysaccharide molecule being conjugated to a single carrier protein). In another embodiment, the capsular polysaccharides not conjugated to the first carrier protein are conjugated to two or more carrier proteins (each capsular polysaccharide molecule being conjugated to a single carrier protein). In such embodiments, each capsular polysaccharide of the same serotype is typically conjugated to the same carrier protein.

Conjugation

Prior to conjugation, the purified polysaccharides can be chemically activated to make the saccharides capable of reacting with the carrier protein to form an activated polysaccharide. As used herein, the term "activated polysaccharide" refers to a polysaccharide that has been chemically modified as described below to enable conjugation to a linker or a carrier protein. The purified polysaccharides can optionally be connected to a linker. Once activated or connected to a linker, each capsular polysaccharide is separately conjugated to a carrier protein to form a glycoconjugate. The polysaccharide conjugates may be prepared by known coupling techniques.

In certain embodiments, the activation of *S. pneumoniae* serotype 23A polysaccharide occurs on the α-Rhap or β-Glcp. In certain embodiments, the activation of *S. pneumoniae* serotype 23B polysaccharide occurs on the β-Glcp or β-Rhap. In one aspect of this embodiment, activation of serotype 23B polysaccharide occurs at greater than 90%, 95%, 99%, or 100% on the β-Rhap. Surprisingly, despite the availability of a suitable activation site on β-Glcp, activation occurs exclusively on the β-Rhap. In certain embodiments, the polysaccharide is activated with periodate. In certain aspects of this embodiment, the activation of serotype 23A polysaccharide occurs on the $2^{nd}$ or $3^{rd}$ carbon position of α-Rhap or β-Glcp or the activation of serotype 23B polysaccharide occurs on the $2^{nd}$ or $3^{rd}$ carbon position of β-Glcp or β-Rhap. In one sub-aspect of this aspect, the extent of activation of serotype 23B polysaccharide on the $2^{nd}$ or $3^{rd}$ carbon position of β-Rhap is greater than the extent of activation on the $2^{nd}$ or $3^{rd}$ carbon position of β-Glcp. The extent of activation on β-Rhap can be at least 60%, 70%, 80%, or 90%. In another sub-aspect of this aspect, perodiate activation of serotype 23B polysaccharide occurs at greater than 90%, 95%, 99% or 100% on the β-Rhap.

In certain embodiments, the polysaccharide can be coupled to a linker to form a polysaccharide-linker intermediate in which the free terminus of the linker is an ester group. The linker is therefore one in which at least one terminus is an ester group. The other terminus is selected so that it can react with the polysaccharide to form the polysaccharide-linker intermediate.

In certain embodiments, the polysaccharide can be coupled to a linker using a primary amine group in the polysaccharide. In this case, the linker typically has an ester group at both termini. This allows the coupling to take place by reacting one of the ester groups with the primary amine group in the polysaccharide by nucleophilic acyl substitution. The reaction results in a polysaccharide-linker intermediate in which the polysaccharide is coupled to the linker via an amide linkage. The linker is therefore a bifunctional linker that provides a first ester group for reacting with the primary amine group in the polysaccharide and a second ester group for reacting with the primary amine group in the carrier molecule. A typical linker is adipic acid N-hydroxysuccinimide diester (SIDEA).

In certain embodiments, the coupling can also take place indirectly, i.e. with an additional linker that is used to derivatise the polysaccharide prior to coupling to the linker. The polysaccharide is coupled to the additional linker using a carbonyl group at the reducing terminus of the polysaccharide. This coupling comprises two steps: (a1) reacting the carbonyl group with the additional linker; and (a2) reacting the free terminus of the additional linker with the linker. In these embodiments, the additional linker typically has a primary amine group at both termini, thereby allowing step (a1) to take place by reacting one of the primary amine groups with the carbonyl group in the polysaccharide by reductive amination. A primary amine group is used that is reactive with the carbonyl group in the polysaccharide. Hydrazide or hydroxylamino groups are suitable. The same primary amine group is typically present at both termini of the additional linker. The reaction results in a polysaccharide-additional linker intermediate in which the polysaccharide is coupled to the additional linker via a C—N linkage.

In certain embodiments, the polysaccharide can be coupled to the additional linker using a different group in the polysaccharide, particularly a carboxyl group. This coupling comprises two steps: (a1) reacting the group with the additional linker; and (a2) reacting the free terminus of the additional linker with the linker. In this case, the additional linker typically has a primary amine group at both termini, thereby allowing step (a1) to take place by reacting one of the primary amine groups with the carboxyl group in the polysaccharide by EDAC activation. A primary amine group is used that is reactive with the EDAC-activated carboxyl group in the polysaccharide. A hydrazide group is suitable. The same primary amine group is typically present at both termini of the additional linker. The reaction results in a polysaccharide-additional linker intermediate in which the polysaccharide is coupled to the additional linker via an amide linkage.

In one embodiment, the chemical activation of the polysaccharides and subsequent conjugation to the carrier protein by reductive amination can be achieved by means described in U.S. Pat. Nos. 4,365,170, 4,673,574 and 4,902,506, U.S. Patent Application Publication Nos. 2006/0228380, 2007/184072, 2007/0231340 and 2007/0184071, and International Patent Application Publication Nos. WO2006/110381, WO2008/079653, and WO2008/143709). The chemistry may entail the activation of pneumococcal polysaccharide by reaction with any oxidizing agent which a primary hydroxyl group to an aldehyde, such as TEMPO in the presence of oxidant (WO2104/097099), or reacting two vicinal hydroxyl groups to aldehydes, such as periodate (including sodium periodate, potassium periodate, or periodic acid). The reactions lead to a random oxidation of primary hydroxyl groups or random oxidative cleavage of vicinal hydroxyl groups of the carbohydrates with the formation of reactive aldehyde groups.

In this embodiment, coupling to the carrier protein is by reductive amination via direct amination to the lysyl groups of the protein. For example, conjugation is carried out by reacting a mixture of the activated polysaccharide and carrier protein with a reducing agent such as sodium cyanoborohydride in the presence of nickel. The conjugation reaction may take place under aqueous solution or in the presence of dimethyl sulfoxide (DMSO). See, e.g., U.S. Patent Application Publication Nos. US2015/0231270 and US2011/0195086 and European Patent No. EP 0471 177 B1. Unreacted aldehydes are then capped with the addition of a strong reducing agent, such as sodium borohydride.

Reductive amination involves two steps, (1) oxidation of the polysaccharide to form reactive aldehydes, (2) reduction of the imine (Schiff base) formed between activated polysaccharide and a carrier protein to form a stable amine conjugate bond. Before oxidation, the polysaccharide is optionally size reduced. Mechanical methods (e.g. homogenization) or chemical hydrolysis may be employed. Chemical hydrolysis may be conducted using acetic acid. The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and includes the various salts of periodate (e.g., sodium periodate and potassium periodate). In an embodiment the capsular polysaccharide is oxidized in the presence of metaperiodate, preferably in the presence of sodium periodate ($NaIO_4$). In another embodiment the capsular polysaccharide is oxydized in the presence of orthoperiodate, preferably in the presence of periodic acid.

In an embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls (as described in, for example, International Patent Application Publication No. WO 2014/097099). In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from the group consisting of N-Chloro-Succinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

In certain aspects, the oxidizing agent is 2,2,6,6-Tetramethyl-1-piperidinyloxy (TEMPO) free radical and N-Chlorosuccinimide (NCS) as the cooxidant (as described in International Patent Application Publication No. WO2014/097099). Therefore in one aspect, the glycoconjugates from *S. pneumoniae* are obtainable by a method comprising the steps of: a) reacting a saccharide with 2,2,6,6-tetramethyl-1-piperidinyloxy (TEMPO) and N-chlorosuccinimide (NCS) in an aqueous solvent to produce an activated saccharide; and b) reacting the activated saccharide with a carrier protein comprising one or more amine groups (said method is designated "TEMPO/NCS-reductive amination" thereafter).

Optionally the oxidation reaction is quenched by addition of a quenching agent. The quenching agent may be selected from vicinal diols, 1,2-aminoalcohols, amino acids, glutathione, sulfite, bisulfate, dithionite, metabisulfite, thiosulfate, phosphites, hypophosphites or phosphorous acid (such as glycerol, ethylene glycol, propan-1,2-diol, butan-1,2-diol or butan-2,3-diol, ascorbic acid).

The second step of the conjugation process for reductive amination is the reduction of the imine (Schiff base) bond between activated polysaccharide and a carrier protein to form a stable conjugate bond (so-called reductive amination), using a reducing agent. Reducing agents which are suitable include the cyanoborohydrides (such as sodium cyanoborohydride) or sodium borohydride. In one embodiment the reducing agent is sodium cyanoborohydride.

In certain embodiments of the methods of the invention, the reductive amination reaction is carried out in aprotic solvent (or a mixture of aprotic solvents). In an embodiment, the reduction reaction is carried out in DMSO (dimethyl sulfoxide) or in DMF (dimethylformamide) solvent. The DMSO or DMF solvent may be used to reconstitute the activated polysaccharide and carrier protein, if lyophilized. In one embodiment, the aprotic solvent is DMSO.

At the end of the reduction reaction, there may be unreacted aldehyde groups remaining in the conjugates, which may be capped or quenched using a suitable capping or quenching agent. In one embodiment this capping or quenching agent is sodium borohydride ($NaBH_4$). Suitable alternatives include sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe'PrN—$BH_3$, benzylamine-$BH_3$ or 5-ethyl-2-methylpyridine borane (PEMB) or borohydride exchange resin.

Glycoconjugates prepared using reductive amination in an aprotic solvent are generally used in multivalent pneumococcal conjugate vaccines. Thus, in certain embodiments for multivalent compositions where not all the serotypes are prepared in an aprotic solvent, the reduction reaction for the remaining seroytpes is carried out in aqueous solvent (e.g., selected from PBS (phosphate buffered saline), MES (2-(N-morpholino)ethanesulfonic acid), HEPES, (4-(2-hydroxyethyl)-1-piperazineethanesulfonic acid), Bis-tris, ADA (N-(2-Acetamido)iminodiacetic acid), PIPES (piperazine-N,N'-bis(2-ethanesulfonic acid)), MOPSO (3-Morpholino-2-hydroxypropanesulfonic acid), BES (N,N-bis(2-hydroxyethyl)-2-aminoethanesulfonic acid), MOPS (3-(N-morpholino)propanesulfonic acid), DIPSO (3-Bis(2-hydroxyethyl) amino-2-hydroxypropane-1-sulfonic acid), MOBS (4-(N-morpholino)butanesulfonic acid), HEPPSO (N-(2-Hydroxyethyl)piperazine-N-(2-hydroxypropanesulfonic acid)), POPSO (Piperazine-1,4-bis(2-hydroxy-3-propanesulfonic acid)), TEA (triethanolamine), EPPS (4-(2-Hydroxyethyl)piperazine-1-propanesulfonic acid), Bicine or HEPB, at a pH between 6.0 and 8.5, 7.0 and 8.0, or 7.0 and 7.5).

In some embodiments, the glycoconjugates of the present invention comprise a polysaccharide having a molecular weight of between 10 kDa and 10,000 kDa. In other such embodiments, the polysaccharide has a molecular weight of between 25 kDa and 5,000 kDa. In other such embodiments, the polysaccharide has a molecular weight of between 50 kDa and 1,000 kDa. In other such embodiments, the polysaccharide has a molecular weight of between 70 kDa and 900 kDa. In other such embodiments, the polysaccharide has a molecular weight of between 100 kDa and 800 kDa. In other such embodiments, the polysaccharide has a molecular weight of between 200 kDa and 600 kDa. In further such embodiments, the polysaccharide has a molecular weight of 100 kDa to 1,000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; or 500 kDa to 600 kDa.

In certain embodiments, the conjugation reaction is performed by reductive amination wherein nickel is used for greater conjugation reaction efficiency and to aid in free cyanide removal. Transition metals are known to form stable complexes with cyanide and are known to improve reductive methylation of protein amino groups and formaldehyde with sodium cyanoborohydride (S Gidley et al., *Biochem J.* 1982, 203: 331-334; Jentoft et al. *Anal Biochem.* 1980, 106: 186-190). By complexing residual, inhibitory cyanide, the addition of nickel increases the consumption of protein during the conjugation of and leads to formation of larger, potentially more immungenic conjugates.

Suitable alternative chemistries include the activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester (optionally made by CDAP chemistry) is coupled with hexane diamine or adipic acid dihydrazide (ADH) and the amino-derivatised saccharide is conjugated to the carrier protein using carbodiimide (e.g. EDAC or EDC) chemistry via a carboxyl group on the protein carrier. Such conjugates are described in International Patent Application Publication Nos. WO 93/15760, WO 95/08348 and WO 96/29094; and Chu et al., 1983, Infect. Immunity 40:245-256.

Other suitable techniques use carbodiimides, hydrazides, active esters, norborane, p-nitrobenzoic acid, N-hydroxysuccinimide, S—NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

Following the conjugation (the reduction reaction and optionally the capping or quenching reaction), the glycoconjugates may be purified (enriched with respect to the amount of polysaccharide-protein conjugate) by a variety of techniques known to the skilled person. These techniques include dialysis, concentration/diafiltration operations, tangential flow filtration, ultrafiltration, precipitation/elution, column chromatography (ion exchange chromatography, multimodal ion exchange chromatography, DEAE, or hydrophobic interaction chromatography), and depth filtration. See, e.g., U.S. Pat. No. 6,146,902. In an embodiment, the glycoconjugates are purified by diafiltration or ion exchange chromatography or size exclusion chromatography.

One way to characterize the glycoconjugates of the invention is by the number of lysine residues in the carrier protein (e.g., CRM197) that become conjugated to the saccharide, which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the glycoconjugate of the invention is about 2, about 3, about 4, about 5, about 6, about 7, about 8, about 9, about 10, about 11, about 12, about 13, about 14 or about 15. In a preferred embodiment, the degree of conjugation of the glycoconjugate of the invention is between 4 and 7. In some such embodiments, the carrier protein is CRM197.

The glycoconjugates of the invention may also be characterized by the ratio (weight/weight) of saccharide to carrier protein. In some embodiments, the ratio of polysaccharide to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of capsular polysaccharide to carrier protein in the conjugate is between 0.9 and 1.1. In some such embodiments, the carrier protein is CRM197. The glycoconjugates and immunogenic compositions of the invention may contain free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate.

In a preferred embodiment, the glycoconjugate comprises less than about 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises less than about 20% of free polysaccharide compared to the total amount of polysaccharide. In a preferred embodiment the glycoconjugate comprises less than about 15% of free polysaccharide compared to the total amount of polysaccharide.

Multivalent Polysaccharide-Protein Conjugate Vaccines

In certain embodiments of the invention, multivalent polysaccharide vaccines comprise unconjugated polysaccharides or polysaccharide-protein conjugates from one or more of Streptococcus pneumoniae serotypes 23A and 23B and capsular polysaccharides from one or more of S. pneumoniae serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18B, 18C, 19A, 19F, 20, 21, 22A, 22F, 23F, 24B, 24F, 27, 28A, 31, 33F, 34, 35A, 35B, 35F, and 38 either as free polysaccharides, a component of a polysaccharide-protein conjugate or a combination thereof, to provide a multivalent pneumococcal vaccine. In certain embodiments of the invention, the immunogenic composition comprises, consists essentially of, or consists of capsular polysaccharides from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 S. pneumoniae serotypes individually conjugated to one or more carrier proteins. Preferably, saccharides from a particular serotype are not conjugated to more than one carrier protein.

After the individual glycoconjugates are purified, they are compounded to formulate the immunogenic composition of the present invention. These pneumococcal conjugates are prepared by separate processes and bulk formulated into a single dosage formulation.

For certain serotypes within S. pneumoniae serogroup 23, cross-protection can be seen. In other words, polysaccharides from a particular serotype may induce an immune response which is protective against another serotype. Typically, the other serotype is within the same serogroup, but in some cases, one serotype may provide protection to a serotype in a different serogroup. On the other hand, sometimes cross-protection is not seen even in the same serogroup with polysaccharides from these serotypes having similar structures. The EXAMPLES unexpectedly demonstrate that polysaccharides from S. pneumoniae serotypes 23A and 23F offer weak cross-protection against S. pneumoniae serotype 23B (while providing robust cross protection against each other). Thus, in order to obtain protection against serotypes 23A, 23B and 23F, a multivalent composition comprising polysaccharide serotypes 23A or 23F needs to include serotype 23B polysaccharide. Accordingly, in certain embodiments of the invention, a multivalent composition comprises polysaccharides from serotypes 23A and 23B. In other embodiments of the invention, a multivalent composition comprises polysaccharides from serotypes 23F and 23B.

Pharmaceutical/Vaccine Compositions

The present invention further provides compositions, including pharmaceutical, immunogenic and vaccine compositions, comprising, consisting essentially of, or alternatively, consisting of any of the polysaccharide S. pneumoniae serotype combinations described above together with a pharmaceutically acceptable carrier and an adjuvant.

Formulation of the polysaccharide-protein conjugates of the present invention can be accomplished using art-recognized methods. For instance, individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In a preferred embodiment, the vaccine composition is formulated in L-histidine buffer with sodium chloride.

As defined herein, an "adjuvant" is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, Mont.) containing 2% Squalene, 0.2% Tween 80, and one or more bacterial cell wall components from the group consisting of 3-O-deacylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA;

(3) saponin adjuvants, such as Quil A or STIMULON™ QS-21 (Antigenics, Framingham, Mass.) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion;

(5) synthetic polynucleotides such as oligonucleotides containing CpG motif(s) (U.S. Pat. No. 6,207,646);

(6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc; and (7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21).

Muramyl peptides include, but are not limited to, N-acetyl-muramyl-L-threonyl-D-isoglutamine (thr-MDP), N-acetyl-normuramyl-L-alanine-2-(1',2'-dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, Alhydrogel®, Superfos, Amphogel®, aluminum (III) hydroxide, aluminum hydroxyphosphate (Aluminum Phosphate Adjuvant (APA)), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and steam sterilized.

In certain embodiments, a commercially available Al(OH)$_3$ (e.g. Alhydrogel® or Superfos of Denmark/Accurate Chemical and Scientific Co., Westbury, N.Y.) is used to adsorb proteins. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of Ag that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

Monovalent bulk aqueous conjugates are typically blended together and diluted. Once diluted, the batch is sterile filtered. Aluminum phosphate adjuvant is added aseptically to target a final concentration of 4 µg/mL for all S. pneumoniae serotypes except serotype 6B, which is diluted to a target of 8 µg/mL, and a final aluminum concentration of 250 µg/mL. The adjuvanted, formulated batch will be filled into vials or syringes.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. In another embodiment, any other art-accepted definition of the terms is intended. CpG-containing oligonucleotides include modified oligonucleotides using any synthetic internucleoside linkages, modified base and/or modified sugar.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

Administration/Dosage

The compositions and formulations of the present invention can be used to protect or treat a human susceptible to infection, e.g., a pneumococcal infection, by means of administering the vaccine via a systemic or mucosal route. In one embodiment, the present invention provides a method of inducing an immune response to a S. pneumoniae capsular polysaccharide conjugate, comprising administering to a human an immunologically effective amount of an immunogenic composition of the present invention. In another embodiment, the present invention provides a method of vaccinating a human against a pneumococcal infection, comprising the step of administering to the human an immunogically effective amount of an immunogenic composition of the present invention.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

"Effective amount" of a composition of the invention refers to a dose required to elicit antibodies that significantly reduce the likelihood or severity of infectivitiy of a microbe, e.g., S. pneumoniae, during a subsequent challenge.

The methods of the invention can be used for the prevention and/or reduction of primary clinical syndromes caused by microbes, e.g., S. pneumoniae, including both invasive infections (meningitis, pneumonia, and bacteremia), and noninvasive infections (acute otitis media, and sinusitis).

Administration of the compositions of the invention can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, for polysaccharide-based conjugates, each dose will comprise 0.1 to 100 μg of each polysaccharide, particularly 0.1 to 10 μg, and more particularly 1 to 5 μg. For example, each dose can comprise 100, 150, 200, 250, 300, 400, 500, or 750 ng or 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 μg of each polysaccharide.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

In one embodiment, the dose of the aluminum salt is 10, 15, 20, 25, 30, 50, 70, 100, 125, 150, 200, 300, 500, or 700 μg, or 1, 1.2, 1.5, 2, 3, 5 mg or more. In yet another embodiment, the dose of aluminum salt described above is per μg of recombinant protein.

Generally, each 0.5 mL dose is formulated to contain: 2 μg of each S. pneumoniae polysaccharide, except for serotype 6B polysaccharide at 4 μg; about 32 μg CRM197 carrier protein (e.g., 32 μg±5 μg, ±3 μg, ±2 μg, or ±1 μg); 0.125 mg of elemental aluminum (0.5 mg aluminum phosphate) adjuvant; and sodium chloride and L-histidine buffer. The sodium chloride concentration is about 150 mM (e.g., 150 mM±25 mM, ±20 mM, ±15 mM, ±10 mM, or ±5 mM) and about 20 mM (e.g., 20 mM±5 mM, ±2.5 mM, ±2 mM, ±1 mM, or ±0.5 mM) L-histidine buffer.

According to any of the methods of the present invention and in one embodiment, the subject is human. In certain embodiments, the human patient is an infant (less than 1 year of age), toddler (approximately 12 to 24 months), or young child (approximately 2 to 5 years). In other embodiments, the human patient is an elderly patient (>65 years). The compositions of this invention are also suitable for use with older children, adolescents and adults (e.g., aged 18 to 45 years or 18 to 65 years).

In one embodiment of the methods of the present invention, a composition of the present invention is administered as a single inoculation. In another embodiment, the composition is administered twice, three times or four times or more, adequately spaced apart. For example, the composition may be administered at 1, 2, 3, 4, 5, or 6 month intervals or any combination thereof. The immunization schedule can follow that designated for pneumococcal vaccines. For example, the routine schedule for infants and toddlers against invasive disease caused by S. pneumoniae is 2, 4, 6 and 12-15 months of age. Thus, in a preferred embodiment, the composition is administered as a 4-dose series at 2, 4, 6, and 12-15 months of age.

The compositions of this invention may also include one or more proteins from S. pneumoniae. Examples of S. pneumoniae proteins suitable for inclusion include those identified in International Patent Application Publication Nos. WO 02/083855 and WO 02/053761.

Formulations

The compositions of the invention can be administered to a subject by one or more method known to a person skilled in the art, such as parenterally, transmucosally, transdermally, intramuscularly, intravenously, intra-dermally, intranasally, subcutaneously, intra-peritonealy, and formulated accordingly.

In one embodiment, compositions of the present invention are administered via epidermal injection, intramuscular injection, intravenous, intra-arterial, subcutaneous injection, or intra-respiratory mucosal injection of a liquid preparation. Liquid formulations for injection include solutions and the like.

The composition of the invention can be formulated as single dose vials, multi-dose vials or as pre-filled syringes.

In another embodiment, compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or non-aqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. However, it is often preferred that a pharmaceutical composition for infusion or injection is essentially isotonic when it is administered. Hence, for storage the pharmaceutical composition may preferably be isotonic or hypertonic. If the pharmaceutical composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to NaCl, $CaCl_2$, KCl and $MgCl_2$. Examples of non-ionic isotonic agents include but are not limited to sucrose, trehalose, mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may for example be selected from the group consisting of Tris, acetate, glutamate, lactate, maleate, tartrate, phosphate, citrate, carbonate, glycinate, L-histidine, glycine, succinate and triethanolamine buffer.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and Tris.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, Polysorbate 80 (PS-80), Polysorbate 20 (PS-20), and Poloxamer 188 (P188) are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations may also contain a surfactant. Preferred surfactants include, but are not limited to: the polyoxyethylene sorbitan esters surfactants (commonly referred to as the Tweens), especially PS-20 and PS-80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. A preferred surfactant for including in the emulsion is PS-20 or PS-80.

Mixtures of surfactants can be used, e.g. PS-80/Span 85 mixtures. A combination of a polyoxyethylene sorbitan ester such as polyoxyethylene sorbitan monooleate (PS-80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants are: polyoxyethylene sorbitan esters (such as PS-80) 0.01 to 1% w/v, in particular about 0.1% w/v; octyl- or nonylphenoxy polyoxyethanols (such as Triton X-100, or other detergents in the Triton series) 0.001 to 0.1% w/v, in particular 0.005 to 0.02% w/v; polyoxyethylene ethers (such as laureth 9) 0.1 to 20% w/v, preferably 0.1 to 10% w/v and in particular 0.1 to 1% w/v or about 0.5% w/v.

In certain embodiments, the composition consists essentially of L-histidine (20 mM), saline (150 mM) and 0.2% w/v PS-20 at a pH of 5.8 with 250 µg/mL of APA (Aluminum Phosphate Adjuvant). PS-20 can range from 0.005 to 0.1% w/v with the presence of PS-20 or PS-80 in formulation controlling aggregation during simulated manufacture and in shipping using primary packaging. Process consists of combining blend of up to 44 S. pneumoniae polysaccharide serotypes in L-histidine, sodium chloride, and PS-20 then combining this blended material with APA and sodium chloride with or without antimicrobial preservatives.

The choice of surfactant may need to be optimized for different drug products and drug substances. For multivalent vaccines containing 15 or more S. pneumoniae polysaccharide serotypes, PS-20 and P188 are preferred. The choice of chemistry used to prepare the conjugate can also influence the stabilization of the formulation. In particular, as exemplified below, pneumococcal polysaccharide-protein conjugates prepared in aqueous or DMSO solvent and combined in a multivalent composition show significant differences in stability depending on the particular surfactant systems used for formulation.

For the formulations described herein, a poloxamer generally has a molecular weight in the range from 1,100 Da to 17,400 Da, from 7,500 Da to 15,000 Da, or from 7,500 Da to 10,000 Da. The poloxamer can be selected from poloxamer 188 or poloxamer 407. The final concentration of the poloxamer in the formulations of the invention is from 0.001 to 5% w/v, or 0.025 to 1% w/v. A surfactant system comprising a poloxamer must further comprise a polyol. In certain aspects, the polyol is propylene glycol and is at final concentration from 1 to 20% w/v. In certain aspects, the polyol is polyethylene glycol 400 and is at final concentration from 1 to 20% w/v.

Suitable polyols for the formulations are polymeric polyols, particularly polyether diols including, but are not limited to, propylene glycol and polyethylene glycol, Polyethylene glycol monomethyl ethers. Propylene glycol is available in a range of molecular weights of the monomer from ~425 Da to ~2,700 Da. Polyethylene glycol and Polyethylene glycol monomethyl ether is also available in a range of molecular weights ranging from ~200 Da to ~35,000 Da including but not limited to PEG200, PEG300, PEG400, PEG1000, PEG MME 550, PEG MME 600, PEG MME 2000, PEG MME 3350 and PEG MME 4000. A preferred polyethylene glycol is polyethylene glycol 400. The final concentration of the polyol in the formulations may be 1 to 20% w/v or 6 to 20% w/v.

The formulation also contains a pH-buffered saline solution. The buffer may, for example, be selected from the group consisting of Tris, acetate, glutamate, lactate, maleate, tartrate, phosphate, citrate, carbonate, glycinate, L-histidine, glycine, succinate, HEPES (4-(2-hydroxyethyl)-1-piperazineethanesulfonic acid), MOPS (3-(N-morpholino)propanesulfonic acid), MES (2-(N-morpholino)ethanesulfonic acid) and triethanolamine buffer. The buffer is capable of buffering a solution to a pH in the range of 4 to 10, 5.2 to 7.5, or 5.8 to 7.0. In certain aspects, the buffer selected from the group consisting of phosphate, succinate, L-histidine, MES, MOPS, HEPES, acetate or citrate. The buffer may furthermore, for example, be selected from USP compatible buffers for parenteral use, in particular, when the pharmaceutical formulation is for parenteral use. The concentrations of buffer will range from 1 mM to 50 mM or 5 mM to 50 mM. In certain aspects, the buffer is L-histidine at a final concentration of 5 mM to 50 mM, or succinate at a final concentration of 1 mM to 10 mM. In certain aspects, the L-histidine is at a final concentration of 20 mM±2 mM.

While the saline solution (i.e., a solution containing NaCl) is preferred, other salts suitable for formulation include but are not limited to, $CaCl_2$, KCl and $MgCl_2$ and combinations thereof. Non-ionic isotonic agents including but not limited to sucrose, trehalose, mannitol, sorbitol and glycerol may be used in lieu of a salt. Suitable salt ranges include, but not are limited to 25 mM to 500 mM or 40 mM to 170 mM. In one aspect, the saline is NaCl, optionally present at a concentration from 20 mM to 170 mM.

In a preferred embodiment, the formulations comprise a L-histidine buffer with sodium chloride.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

The compositions of this invention may also include one or more proteins from S. pneumoniae. Examples of S. pneumoniae proteins suitable for inclusion include those identified in International Patent Application Publication Nos. WO 02/083855 and WO 02/053761.

Analytical Methods

Molecular Weight and Concentration Analysis of Conjugates Using HPSEC/UV/MALS/RI Assay Conjugate samples are injected and separated by high performance size-exclusion chromatography (HPSEC). Detection is accomplished with ultraviolet (UV), multi-angle light scattering (MALS) and refractive index (RI) detectors in series. Protein concentration is calculated from UV280 using an extinction coefficient. Polysaccharide concentration is deconvoluted from the RI signal (contributed by both protein and polysaccharide) using the do/dc factors which are the change in a solution's refractive index with a change in the solute concentration reported in mL/g. Average molecular weight of the samples are calculated by Astra software (Wyatt Technology Corporation, Santa Barbara, Calif.) using the measured concentration and light scattering information across the entire sample peak. There are multiple forms of average values of molecular weight for polydispersed molecules. For example, number-average molecular weight Mn, weight-average molecular weight Mw, and z-average molecular weight Mz (Molecules, 2015, 20:10313-10341). Unless specified, the term "molecular weight", as used throughout the specification, is the weight-average molecular weight.

Determination of Lysine Consumption in Conjugated Protein as a Measure of the Number of Covalent Attachments Between Polysaccharide and Carrier Protein The Waters AccQ-Tag amino acid analysis (AAA) is used to measure the extent of conjugation in conjugate samples. Samples are hydrolyzed using vapor phase acid hydrolysis in the Eldex workstation, to break the carrier proteins down into their component amino acids. The free amino acids are derivatized using 6-aminoquinolyl-N-hydroxysuccinimidyl carbamate (AQC). The derivatized samples are then analyzed using UPLC with UV detection on a C18 column. The average protein concentration is obtained using representative amino acids other than lysine. Lysine consumption during conjugation (i.e., lysine loss) is determined by the difference between the average measured amount of lysine in the conjugate and the expected amount of lysine in the starting protein.

Free Polysaccharide Testing

Free polysaccharide (i.e., polysaccharide that is not conjugated with CRM197) in the conjugate sample is measured by first precipitating free protein and conjugates with deoxycholate (DOC) and hydrochloric acid. Precipitates are then filtered out and the filtrates are analyzed for free polysaccharide concentration by HPSEC/UV/MALS/RI. Free polysaccharide is calculated as a percentage of total polysaccharide measured by HPSEC/UV/MALS/RI.

Free Protein Testing

Free polysaccharide, polysaccharide-CRM197 conjugate, and free CRM197 in the conjugate samples are separated by capillary electrophoresis in micellar electrokinetic chromatography (MEKC) mode. Briefly, samples are mixed with MEKC running buffer containing 25 mM borate, 100 mM SDS, pH 9.3, and are separated in a preconditioned bare-fused silica capillary. Separation is monitored at 200 nm and free CRM197 is quantified with a CRM197 standard curve. Free protein results are reported as a percentage of total protein content determined by the HPSEC/UV/MALS/RI procedure.

Having described various embodiments of the invention with reference to the accompanying description and drawings, it is to be understood that the invention is not limited to those precise embodiments, and that various changes and modifications may be effected therein by one skilled in the art without departing from the scope or spirit of the invention as defined in the appended claims.

The following examples illustrate but do not limit the invention.

EXAMPLES

Example 1

Preparation of S. Pneumoniae Capsular Polysaccharides

Methods of culturing pneumococci are well known in the art. See, e.g., Chase, 1967, Methods of Immunology and Immunochemistry 1:52. Methods of preparing pneumococcal capsular polysaccharides are also well known in the art. See, e.g., European Patent No. EP 0 497 524 B1. The process described below generally follows the method described in European Patent No. EP 0 497 524 B1 and is generally applicable to all pneumococcal serotypes except where specifically modified.

Isolates of pneumococcal subtypes 23A and 23F were obtained from the Merck Culture Collection. Strain for serotype 23B was obtained from Centers for Disease Control and Prevention (Atlanta, Ga.). Where needed, subtypes can be differentiated on the basis of Quelling reaction using specific antisera. See, e.g., U.S. Pat. No. 5,847,112. The obtained isolates were further clonally isolated by plating serially in two stages on agar plates consisting of an animal-component free medium containing soy peptone, yeast extract, and glucose without hemin (except for serotype 23F, which contained hemin). Clonal isolates for each serotype were further expanded in liquid culture using animal-component free media containing soy peptone, yeast extract, HEPES, sodium chloride, sodium bicarbonate, potassium phosphate, glucose, and glycerol to prepare the pre-master cell banks.

The production of each serotype of pneumococcal polysaccharide consisted of a cell expansion and batch production fermentation followed by chemical inactivation prior to downstream purification. For serotypes other than 23F, a thawed cell bank vial from each serotype was expanded using a shake flask or culture bottle containing a pre-sterilized animal-component free growth media containing soy peptone or soy peptone ultrafiltrate, yeast extract or yeast extract ultrafiltrate, HEPES, sodium chloride, sodium bicarbonate, potassium phosphate, and glucose. The cell expansion culture was grown in a sealed shake flask or bottle to minimize gas exchange with temperature and agitation control. For serotype 23F, a thawed calle bank vial was expanded using a fermentor containing the same media. During the cell expansion of serotype 23F, temperature, pH, pressure, and agitation were controlled. Airflow overlay was also controlled as sparging was not used.

After achieving a specified culture density, as measured by optical density at 600 nm, a portion of the cell expansion culture was transferred to a production fermentor containing pre-sterilized animal-component free growth media containing soy peptone or soy peptone ultrafiltrate, yeast extract or yeast extract ultrafiltrate, sodium chloride, potassium phosphate, and glucose. Temperature, pH, pressure, and agitation were controlled. Airflow overlay was also controlled as sparging was not used.

The batch fermentation was terminated via the addition of a chemical inactivating agent, phenol, when glucose was nearly exhausted. Pure phenol was added to a final concentration of 0.8-1.2% to inactivate the cells and liberate the capsular polysaccharide from the cell wall. Primary inactivation occurs for a specified time within the fermentor where temperature and agitation continue are to be controlled. After primary inactivation, the batch was transferred to another vessel where it was held for an additional specified time at controlled temperature and agitation for complete inactivation. This was confirmed by either microbial plating techniques or by verification of the phenol concentration and specified time. The inactivated broth was then purified.

Purification of Ps

The purification of the pneumococcal polysaccharide consisted of several centrifugation, depth filtration, concentration/diafiltration operations, and precipitation steps. All procedures were performed at room temperature unless otherwise specified.

Inactivated broth from the fermentor cultures of *S. pneumoniae* were flocculated with a cationic polymer (such as BPA-1000, Petrolite "Tretolite" and "Spectrum 8160" and poly(ethyleneimine), "Millipore pDADMAC"). The cationic polymers binded to the impurity protein, nucleic acids and cell debris. Following the flocculation step and an aging period, flocculated solids were removed via centrifugation and multiple depth filtration steps. Clarified broth was concentrated and diafiltered using a 100 kDa to 500 kDa MWCO (molecular weight cutoff) filter. Diafiltration was accomplished using Tris, $MgCl_2$ buffer and sodium phosphate buffer. Diafiltration removed residual nucleic acid and protein.

Further impurities removal was accomplished by reprecipitation of the polysaccharide in sodium acetate and phenol with denatured alcohol and/or isopropanol. During the phenol precipitation step, sodium acetate in sodium phosphate saline buffer and phenol (liquefied phenols or solid phenols) was charged to the diafiltered retentate. Alcohol fractionation of the polysaccharide was then conducted in two stages. In the first stage a low percent alcohol was added to the preparation to precipitate cellular debris and other unwanted impurities, while the crude polysaccharide remained in solution. The impurities were removed via centrifugation followed by a depth filtration step. The polysaccharide was then recovered from the solution by adding additional isopropanol or denatured alcohol to the batch. The precipitated polysaccharide pellet was recovered by centrifugation, triturated and dried as a powder and stored frozen at −70° C.

Example 2

NMR Structure Analyses of Polysaccharides

The strategy for determining polysaccharide structure involved a multiple step process performed substantially as described in Abeygunawardana et al., Determination of the Chemical Structure of Complex Polysaccharides by Heteronuclear NMR Spectroscopy in Advances in Biophysical Chemistry 1993, Vol 3, pages 199-249, JAI Press Inc. The purified polysaccharides were examined using standard 1D and 2D NMR techniques. Finally, the polysaccharides were examined for the presence of phosphate using $^{31}P$ NMR.

Assignments of the monosaccharide residues were carried out through $^1H$-$^1H$ COSY, double quantum filtered homonuclear COSY and total correlation spectroscopy (TOCSY). $^{13}C$ chemical shifts were assigned by heteronuclear single quantum coherence spectroscopy (HSQC) and combination HSQC-TOCSY. Multiplicity-edited HSQC was used to distinguish methylene from methine groups. Inter-residue linkages were determined through a combination of HMBC and NOESY spectroscopy. The anomeric configuration of the residues was determined from the anomeric proton and carbon chemical shifts, $^3J_{H1,H2}$ and $^1J_{H1,C1}$ values.

1D Phosphorus NMR spectroscopy indicated *S. pneumoniae* serotypes 23A and 23B polysaccharides contained phosphorus in the structure. Assignment of the phosphorus linkage site was determined through $^1H$-$^{31}P$ HMBC.

Based on the NMR data in FIGS. 2-5, the structure for *S. pneumoniae* serotype 23A polysaccharide was determined to be as follows:

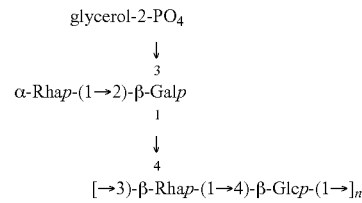

wherein n represents the number of repeating units constituting the polysaccharide. See also FIG. 1A.

Based on the NMR data in FIGS. 2-5, the structure for *S. pneumoniae* serotype 23B polysaccharide was determined to be as follows:

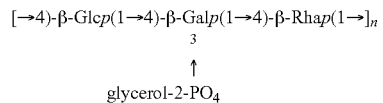

wherein n represents the number of repeating units constituting the polysaccharide. See also FIG. 1B.

The sugar residues for *S. pneumoniae* serotype 23A and 23B polysaccharides include rhamnose (Rha), galactose (Gal), glucose (Glc) and glycerol.

The italicized letters (p and f) refer to pyranose (a closed ring consisting of six atoms) and furanose (a closed ring consisting of five atoms).

The α and β refer to the configuration of the proton attached to anomeric carbon of the sugar unit. The anomeric carbon is always number 1 when labeling the carbon atom in a sugar unit (usually 1 through 6). α means the anomeric proton is in the equatorial position in the 3D structure. β means the anomeric proton is in the axial position.

The numbers associated with arrows refer to how the individual sugar units are connected to each other. For example, the nomenclature α-Rhap-(1→3)-α-Glcp- means the number 1 carbon of Rhamnose is linked to the number 3 carbon of Glucose (p means they are both pyranose rings).

Identification of Activation Sites

Activation sites were identified by reacting the aldehydes (usually hydrated) with thiosemicarbazide (TSC) in 5 mM citrate buffer. TSC reacts with aldehydes (as well as hydrated aldehydes) to form an imine (secondary aldimine). The imine proton formed has a unique chemical shift that is downfield of the polysaccharide signals and was used to probe the oxidation sites of the polysaccharide.

Oxidized *S. pneumoniae* serotype 23B polysaccharide was diluted with sodium citrate buffer then reacted with thiosemicarbazide, mixed continuously at ambient temperature, and then lyophilized. The lyophilized sample was dissolved with 0.9 mL deuterium oxide for NMR analysis.

NMR experiments were carried out at 600 MHz at probe temperature of 25° C. using a cryogenically cooled probe. A 1D proton spectrum was acquired using a 90 degree pulse with 16 transients and a 10 second delay between pulses (including 3 seconds of acquisition time). TOCSY and Gradient COSY data were acquired with 4 transients in the first dimension and 256 and 512 increments in the second dimension respectively. NOESY data were acquired with 16 transients in the first dimension and 256 increments in the second dimension.

Figure 6:
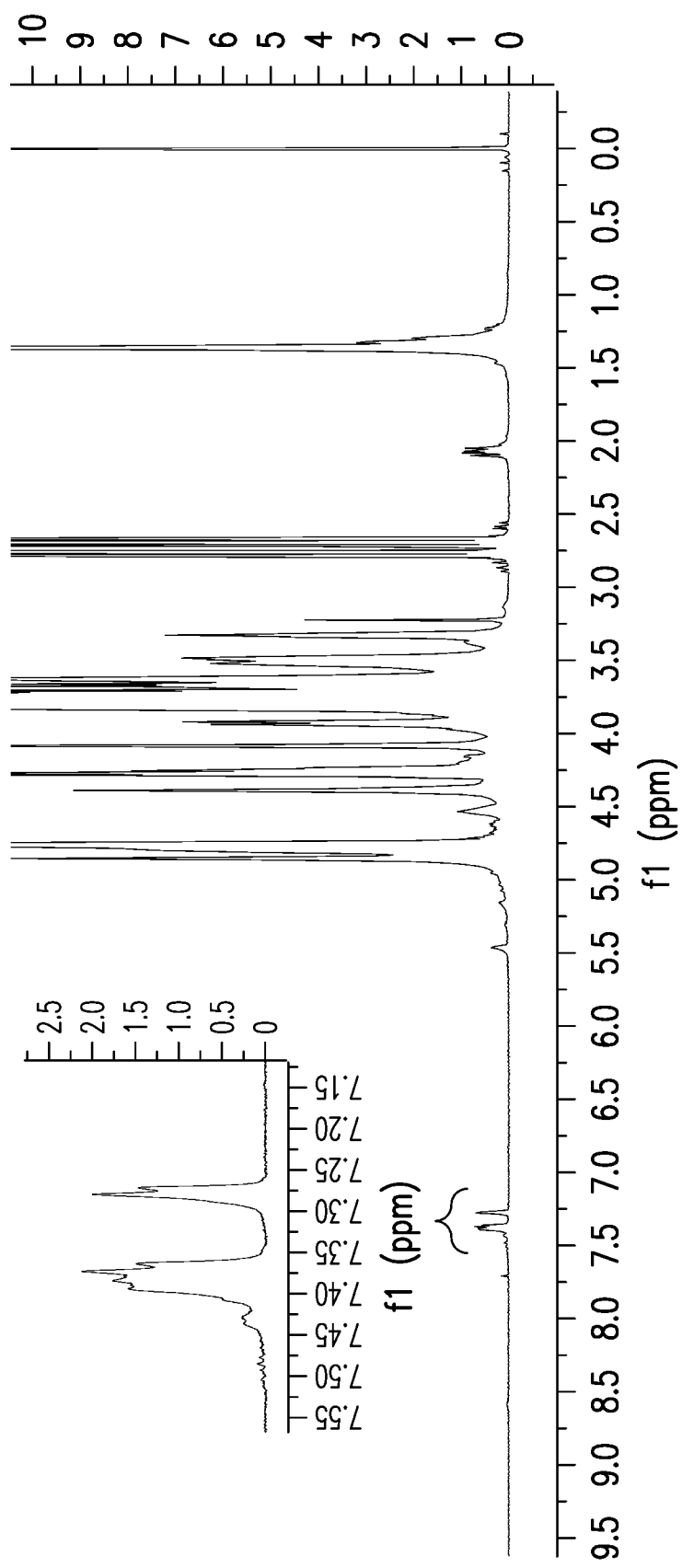
FIG. 6: 600 MHz one-dimensional $^1$H NMR spectrum of oxidized and TSC derivatized capsular polysaccharide from *S. pneumoniae* serotype 23B in deuterium oxide (D$_2$O) at 25° C. The insert is an expansion of the imine signals formed by derivatization with thiosemicarbazide.
Figure 7:
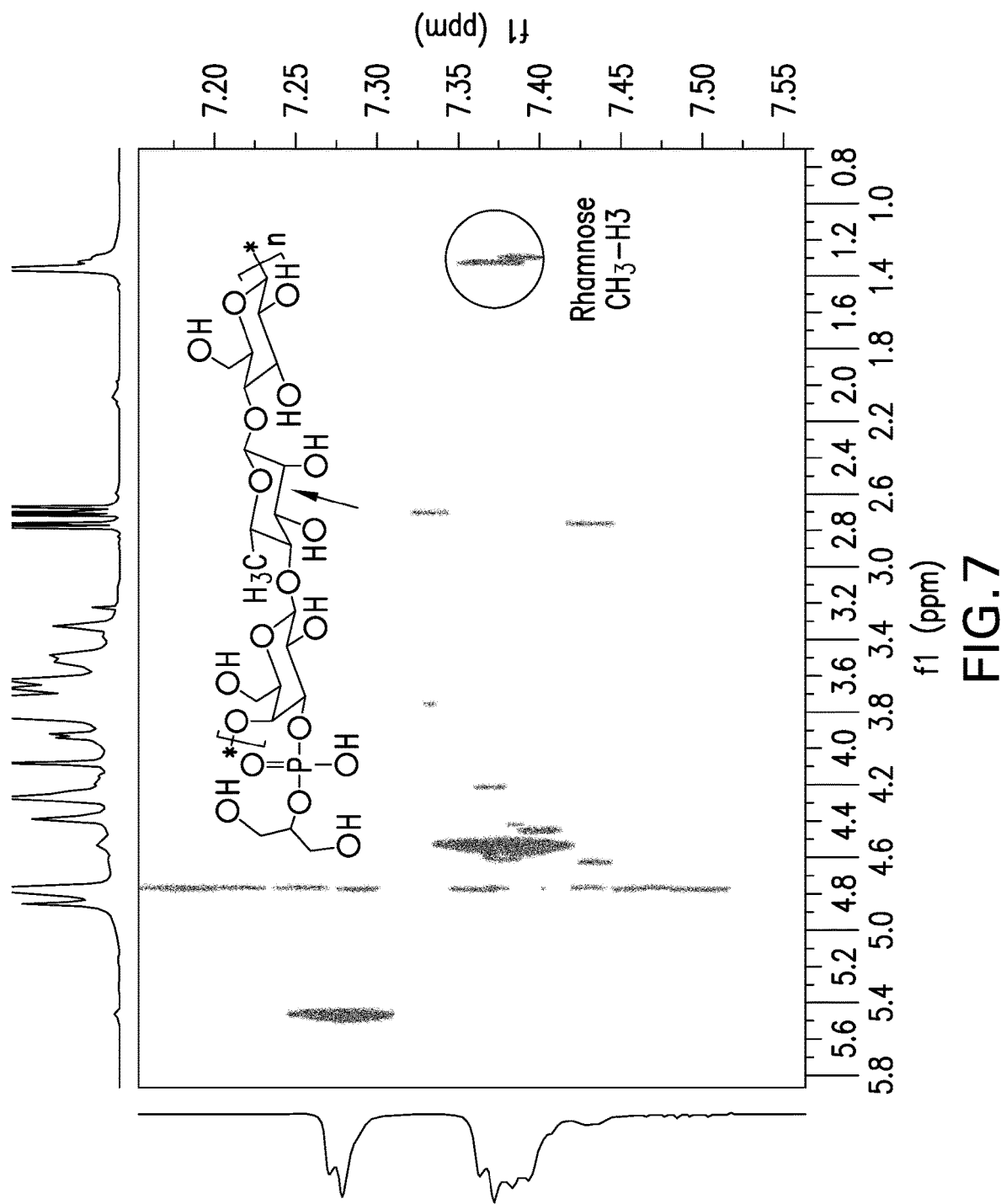
FIG. 7: 2D TOCSY of spectrum of oxidized and TSC derivatized capsular polysaccharide from *S. pneumoniae* serotype 23B. The correlation signals between 7.36-7.40 ppm peaks with rhamnose CH$_3$ peaks (~1.32 ppm) are circled. Insert is the structure for capsular polysaccharide from *S. pneumoniae* serotype 23B, the periodate activation site has been indicated with an arrow.
Figure 8A:
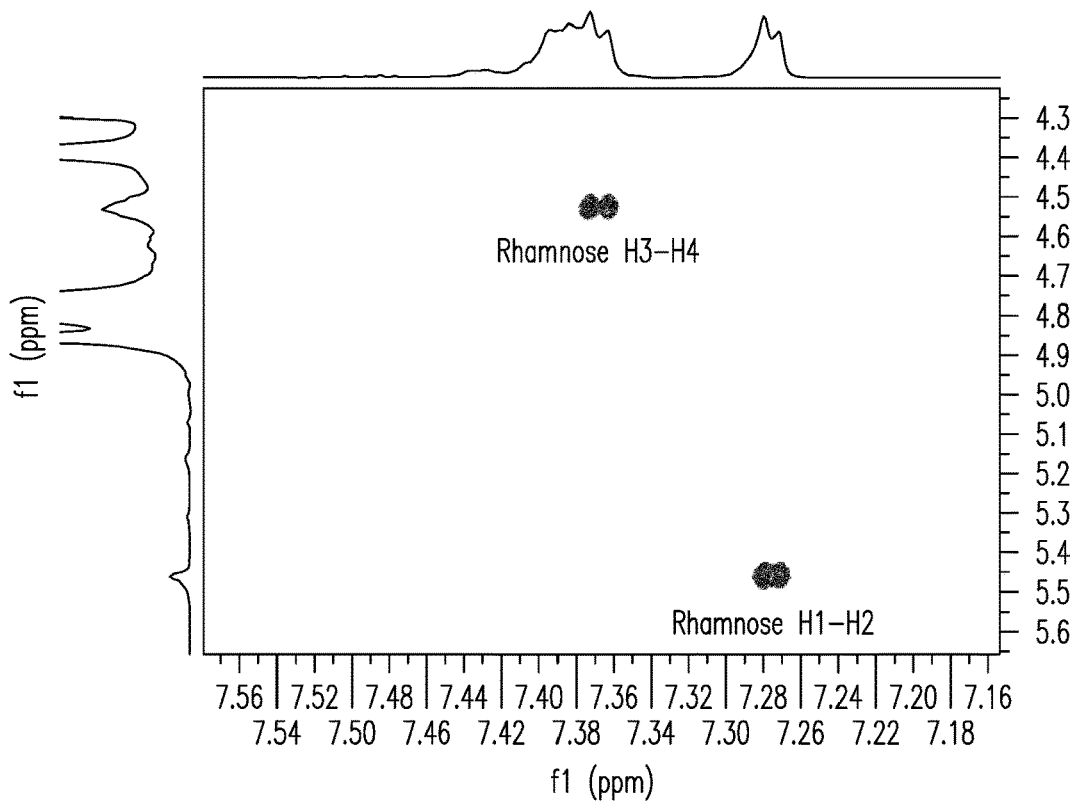
FIG. 8A-B: 2D gCOSY (A) and NOESY (B) of spectrum of oxidized and TSC derivatized capsular polysaccharide from *S. pneumoniae* serotype 23B.
Figure 8B:
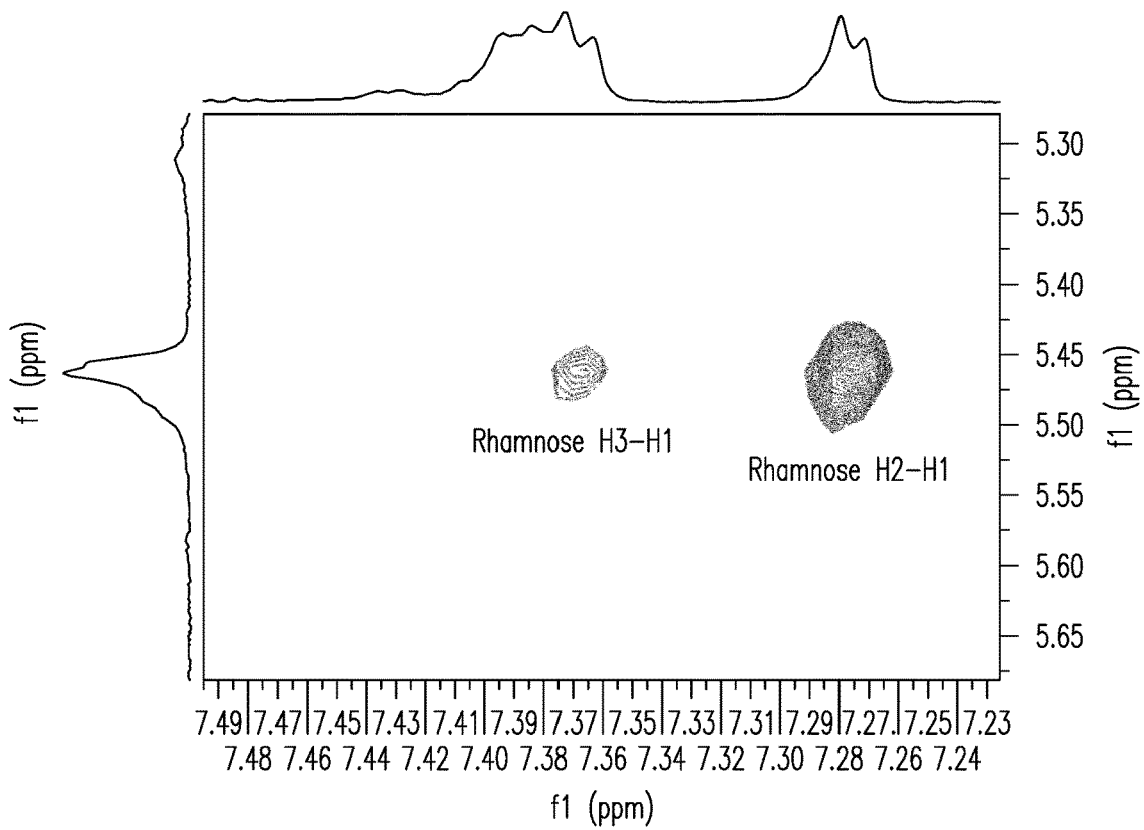

After TSC derivatization, all activated aldehydes were transformed to imine. The chemical shift of aldehyde protons were moved to 7-8 ppm, FIG. 6. The experiment result suggested two group of peaks are formed between 7.0 ppm and 7.5 ppm (7.28 ppm and 7.36-7.40 ppm). 2D TOCSY indicated a correlation between the 7.36-7.40 ppm peaks with rhamnose $CH_3$ peaks (~1.32 ppm; FIG. 7), suggesting those peaks (7.36-7.40 ppm) are proton signals of TSC derivatized 23B rhamnose. According to the non-activated serotype 23B polysaccharide structure, the only possible proton for 7.36-7.40 ppm peaks on the rhamnose ring is H3.

gCOSY data indicated the peaks at 5.46 ppm correlate with peaks at 7.28 ppm. NOESY data indicated the peaks at 5.46 ppm are in close proximity with the peak at 7.37 ppm (H3). Those data suggested the peaks at 5.46 ppm belong to TSC derivatized rhamnose H1, and the peaks at 7.28 ppm belong to TSC derivatized rhamnose H2, FIG. 8.

Figure 1B:
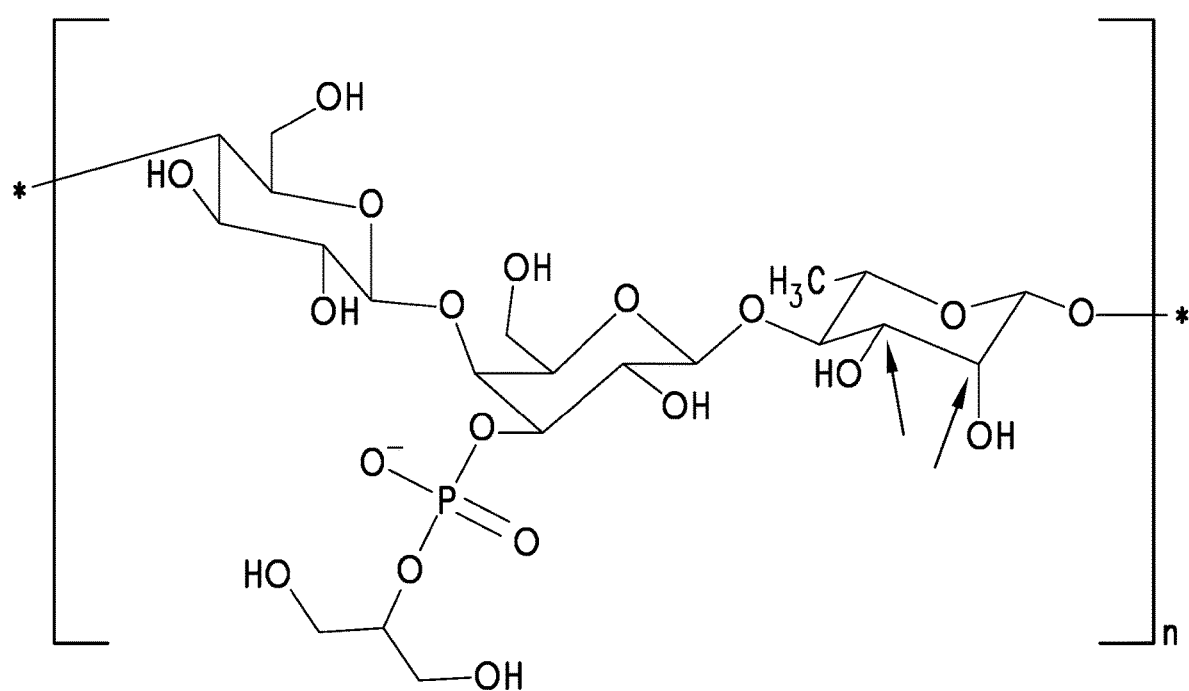
Figure 2A:
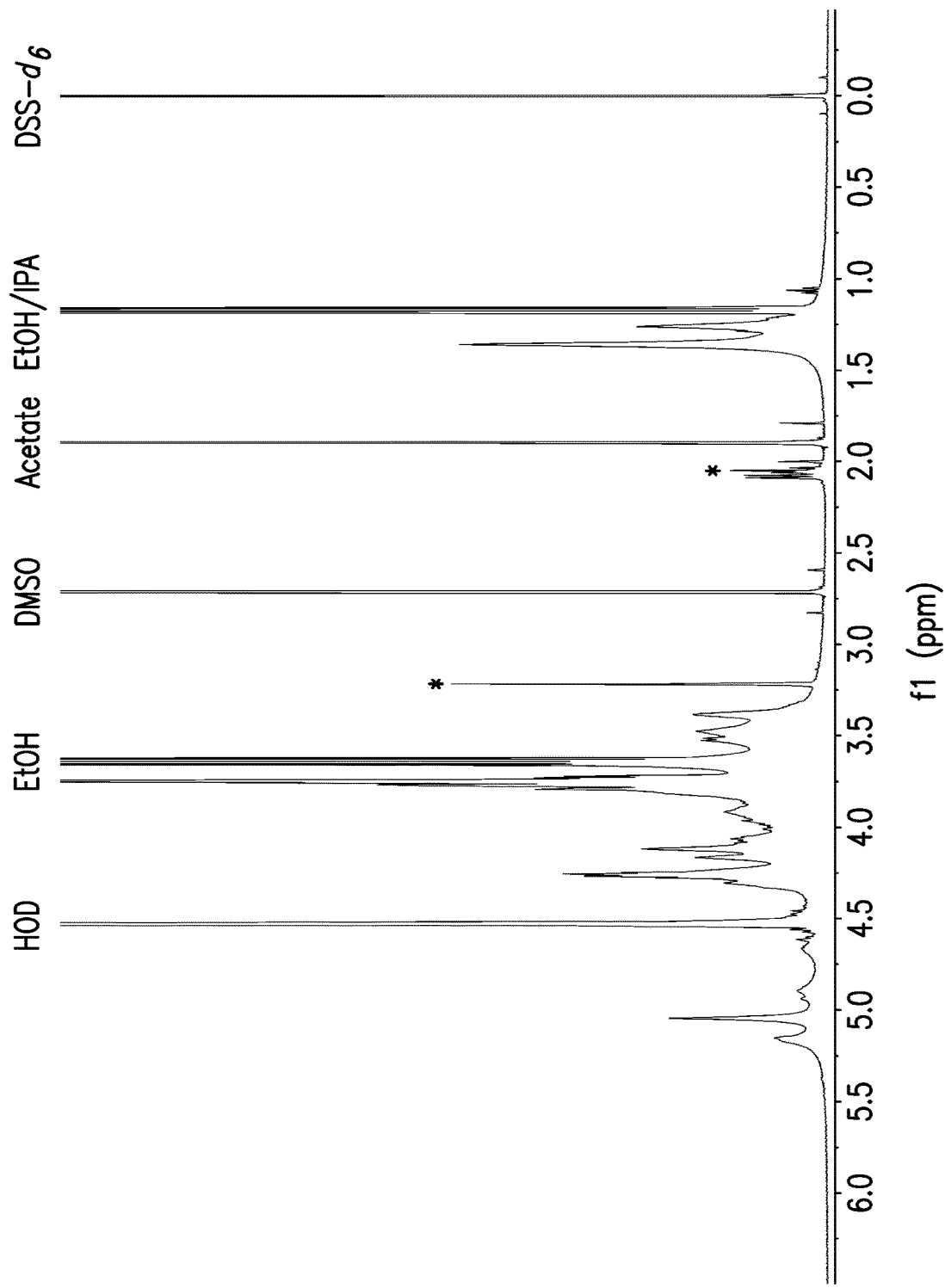
FIG. 2A-B depict the 600 MHz one-dimensional 1H NMR spectrum of the capsular polysaccharide from *S. pneumoniae* serotype 23A (A) and 23B (B) in deuterium oxide (D$_2$O) at 50° C. Signals arising from internal standards (DMSO and DSS-d$_6$), residual water (HOD) and other residual components from the purification process; ethanol (EtOH), isopropanol (IPA) and acetate, are marked. Minor signals marked by * are due to *S. pneumoniae* cell wall residuals such as C-polysaccharide and/or peptidoglycans.
Figure 2B:
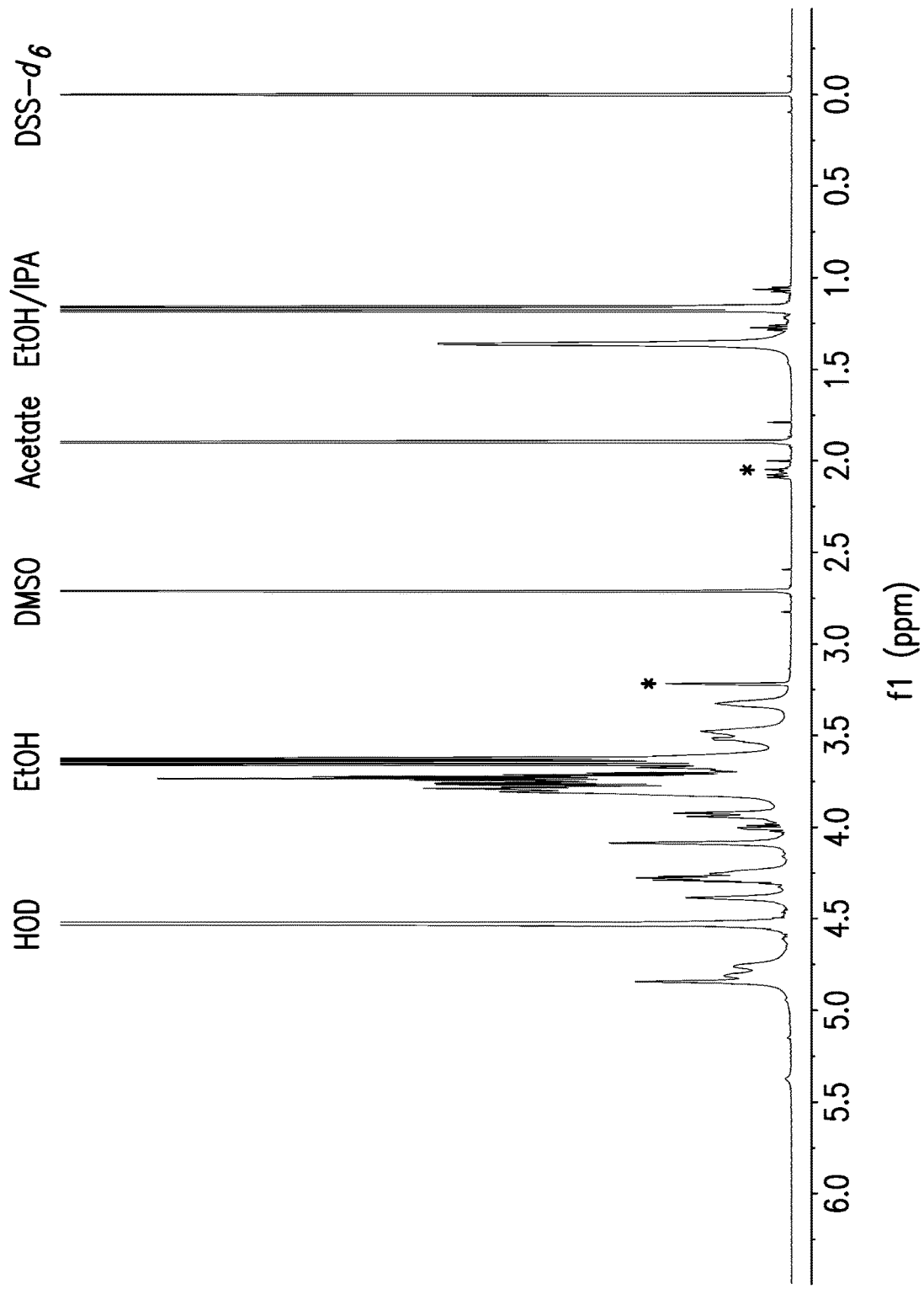
Figure 3A:
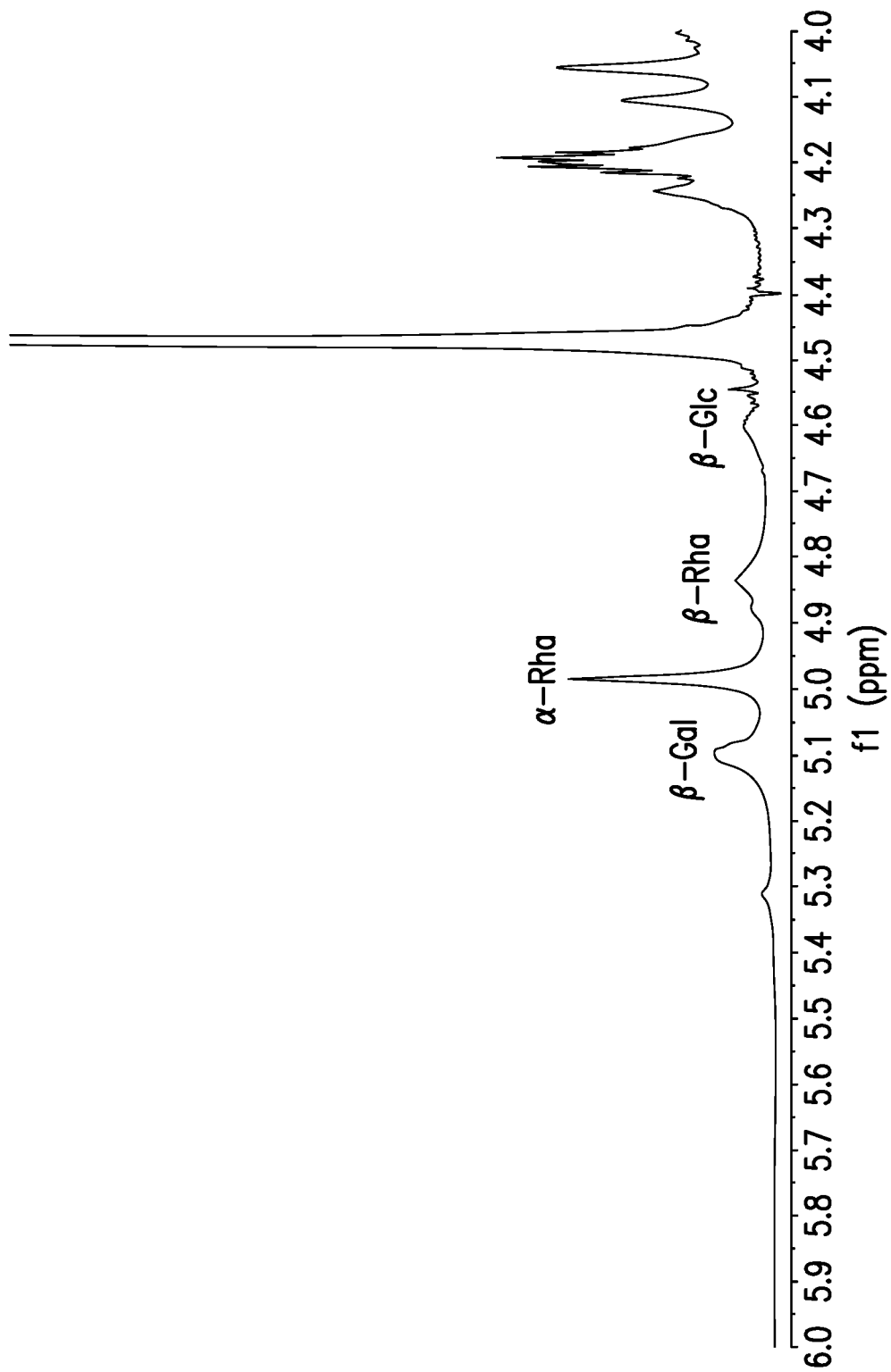
FIGS. 3A-B depict the one-dimensional (1D) $^1$H NMR identity region to be used for serotype identifications of *S. pneumoniae* serotype 23A (A) and 23B (B). Signal positions of each anomeric proton of the repeating unit from each monosaccharide residue is marked.
Figure 3B:
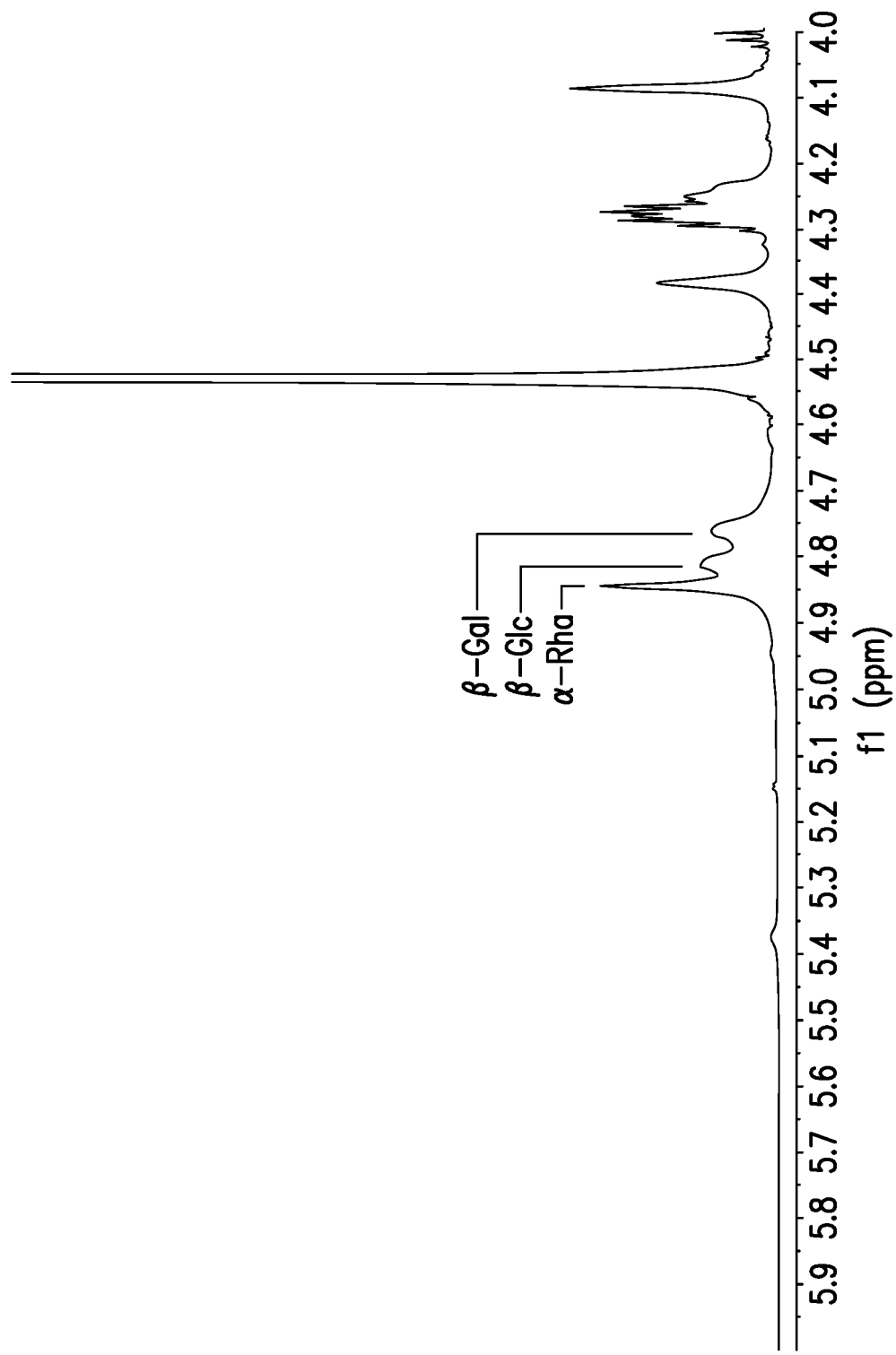
Figure 4A:
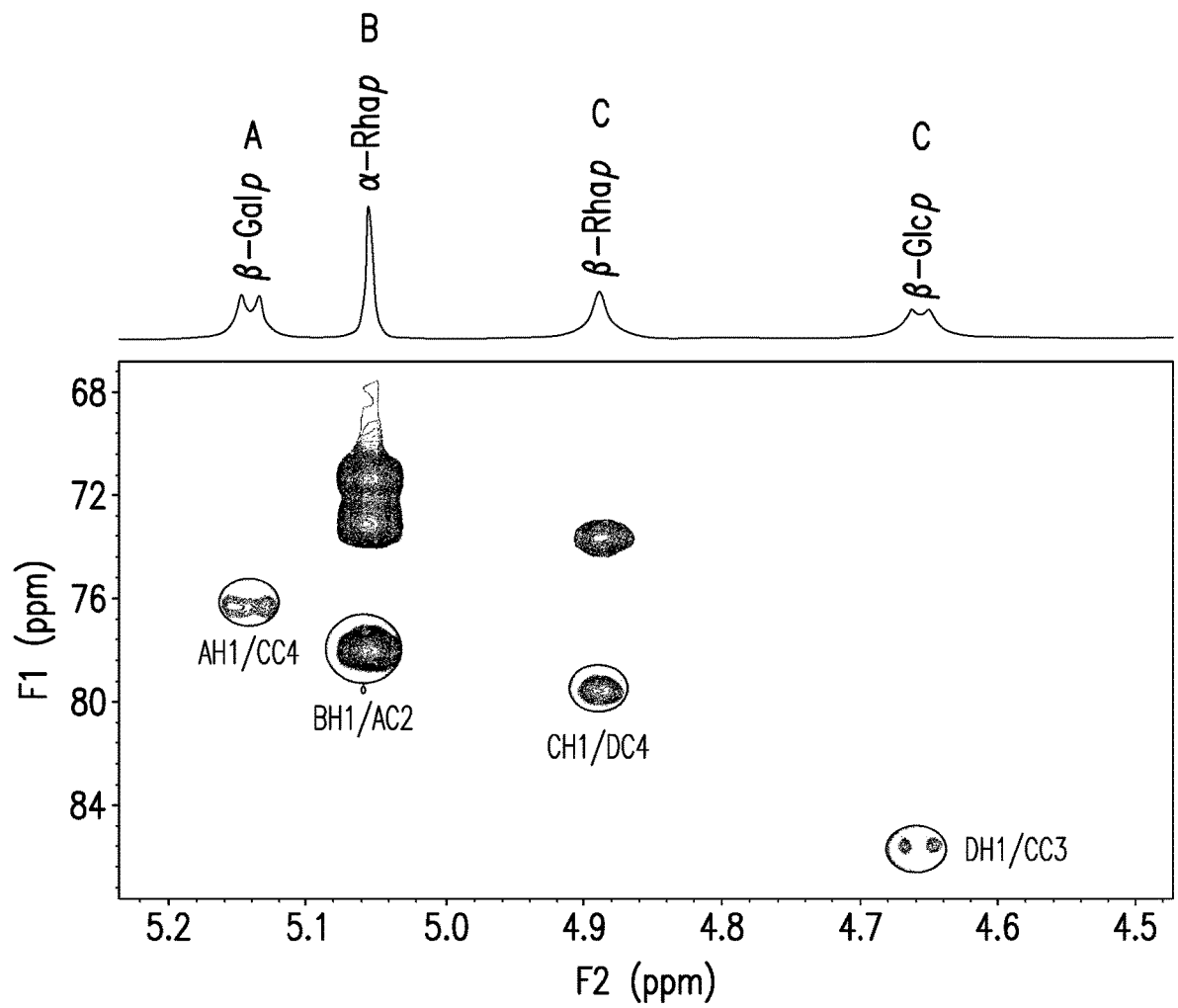
FIGS. 4A-B depict partial two-dimensional (2D) $^1$H-$^{13}$C multiple bond correlation NMR spectrum of *S. pneumoniae* serotype 23A (A) and 23B (B) establishing covalent linkages between sugar residues in the repeating structure. Correlation establishing glycosidic linkages are labeled in the figure.
Figure 4B:
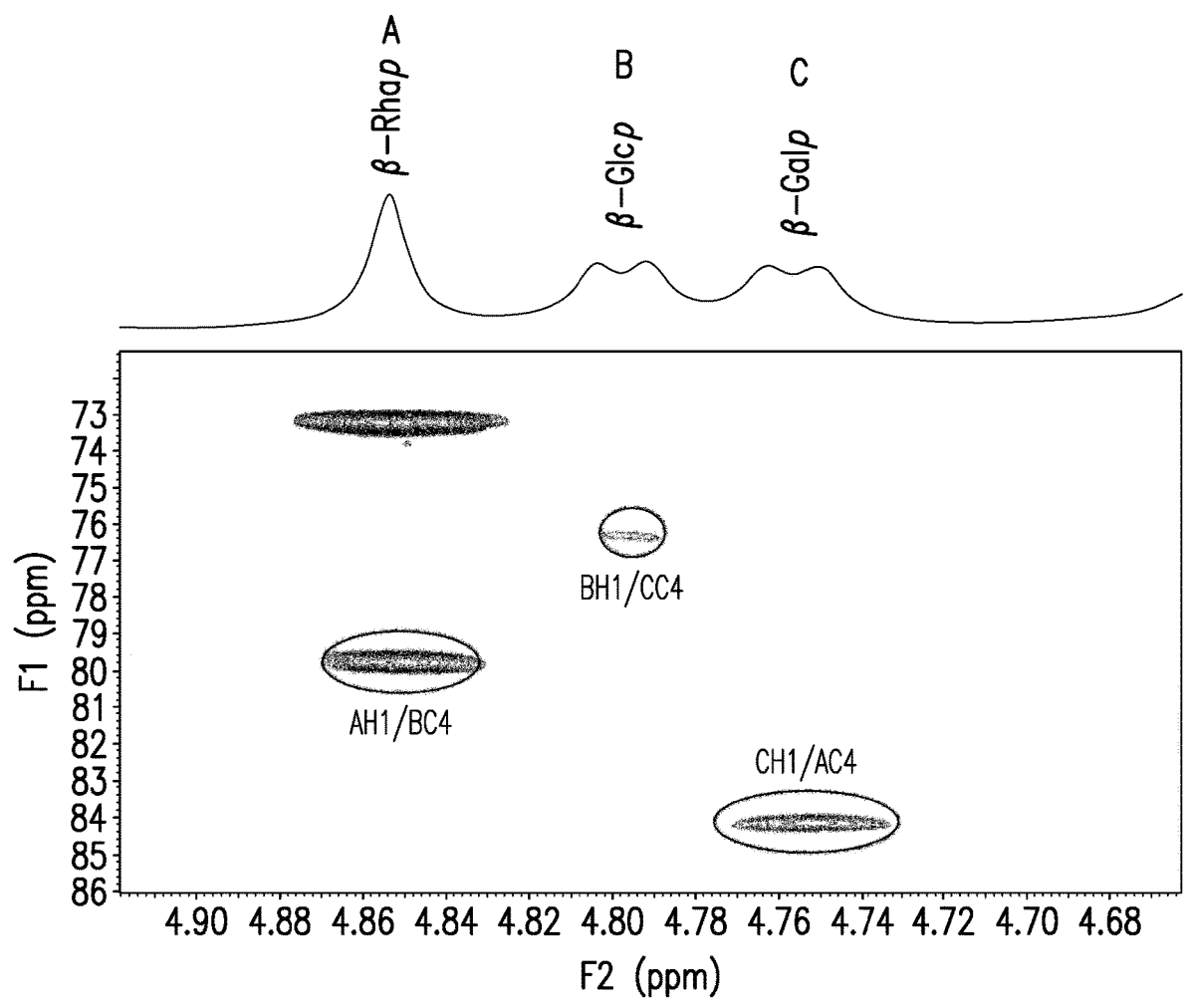
Figure 5A:
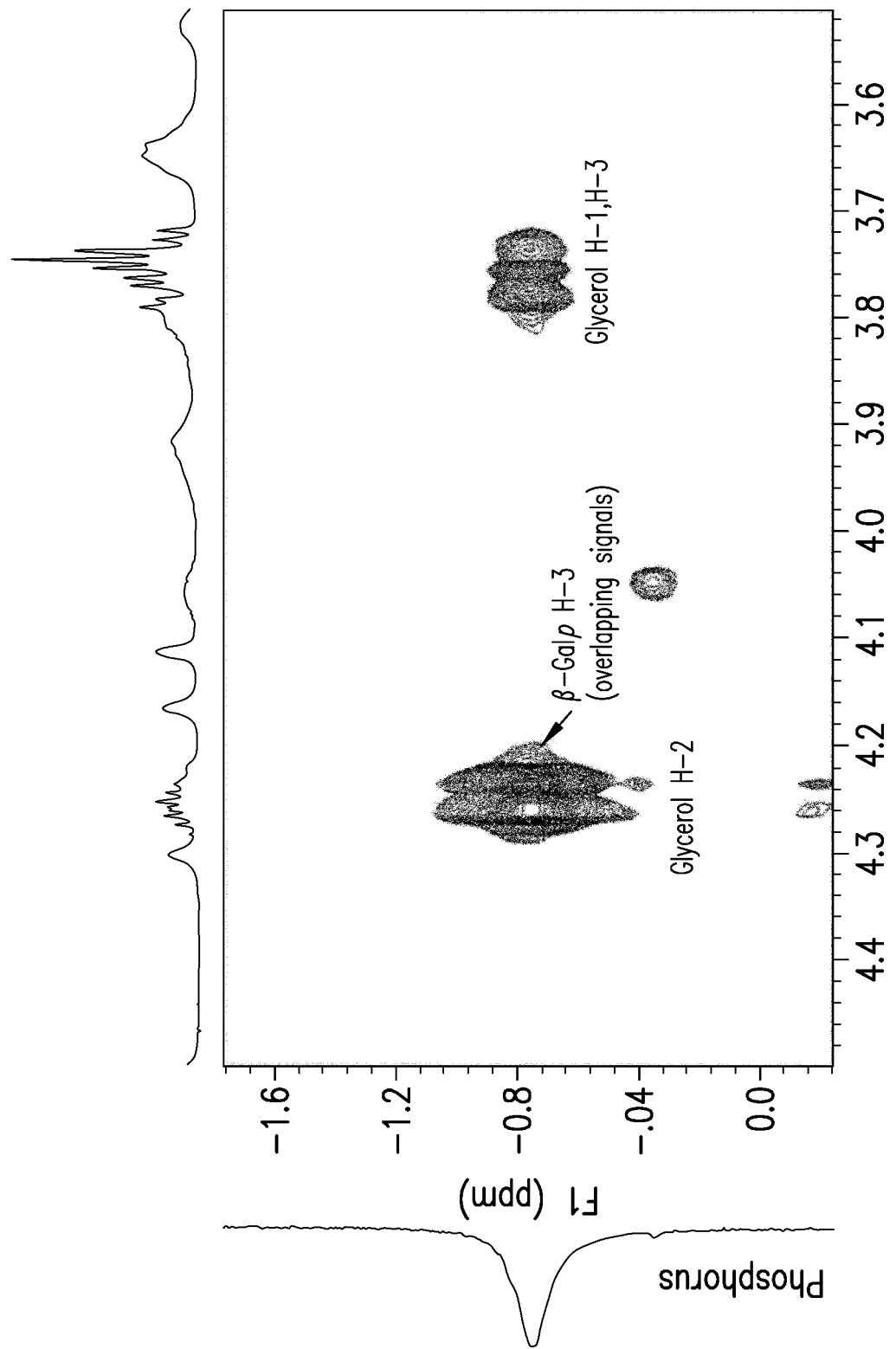
FIGS. 5A-B depicts establishment of phosphodiester linkages in the capsular polysaccharide repeating unit of *S. pneumoniae* serotype 23A (A) and 23B (B).
Figure 5B:
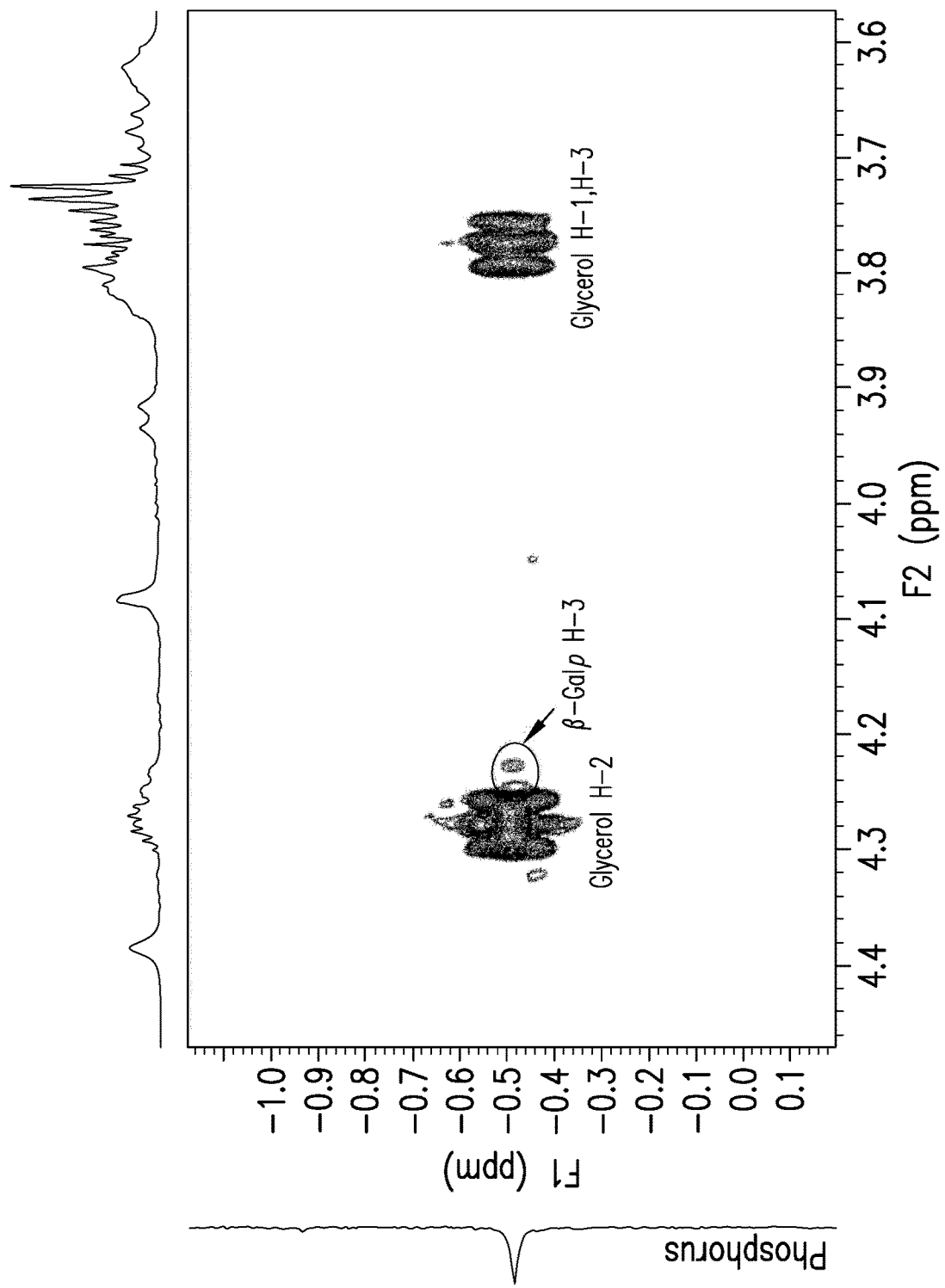

According to the above data, the main activation site for the serotype 23B polysaccharide is at rhamnose C2/C3 position, as indicated in FIG. 1B.

Example 3

Conjugation of *S. Pneumoniae* Serotype 23A Polysaccharide to CRM197 Using Reductive Amination in Dimethylsulfoxide Polysaccharide was dissolved, sized to a target molecular mass, chemically activated and buffer-exchanged by ultrafiltration. Activated polysaccharide and purified CRM197 were individually lyophilized and redissolved in dimethyl sulfoxide (DMSO). Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was either size-reduced by acid hydrolysis or by homogenization. Acid hydrolysis was performed by adding acetic acid to 200 mM, incubating at 90° C. for 1.5 hours, then neutralizing by adding cold potassium phosphate pH 7 buffer to 400 mM. For homogenization, pressure and number of passes through the homogenizer were controlled to 800-1000 bar/5 passes.

Size-reduced polysaccharide was concentrated and diafiltered against water using a 5 NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. The sodium metaperiodate added was 0.20-0.24 moles of sodium metaperiodate per mole of polysaccharide repeating unit to achieve a target level of polysaccharide activation (moles aldehyde per mole of polysaccharide repeating unit). The oxidation reaction proceeded for 2 hours at 22° C.

The activated product was diafiltered against 10 mM potassium phosphate, pH 6.4 followed by diafiltration against water using a 5 kDa NMWCO tangential flow ultrafiltration membrane. Ultrafiltration was conducted at 2-8° C.

Polysaccharide Conjugation to CRM197

Purified CRM197, obtained through expression in *Pseudomonas fluorescens* as previously described (WO 2012/173876 A1), was diafiltered against 2 mM phosphate, pH 7.0 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a concentration of 25-50 mM. The polysaccharide and CRM197 solutions were blended to achieve a polysaccharide concentration of 1.8-3.0 g Ps/L (grams polysaccharide/liter) and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added and conjugation proceeded for 2-4 hours at 22° C.

Reduction with Sodium Borohydride

Sodium borohydride (2 mole per mole of polysaccharide repeating unit) was added following the conjugation reaction and incubated for 1-3 hours at 22° C. The batch was diluted into 150 mM sodium chloride, with approximately 0.025% (w/v) polysorbate 20, at approximately 4° C. Potassium phosphate buffer was then added to neutralize the pH. For some batches, the batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Table 1 shows the attributes of serotype 23A conjugate prepared in DMSO.

TABLE 1

Attributes of S. pneumoniae serotype 23A conjugate from DMSO conjugation

| Oxidized Ps Mw | Conjugate Mw | Ps:Pr | Lysine Consumption (mol/mol CRM197) | Free Ps/ Total Ps | Free Protein/ Total Protein |
|---|---|---|---|---|---|
| 97 kD | 3837 kD | 1.20 | 11.8 | 0.2% | 0.6% |
| 190 kD | 5620 kD | 1.07 | 11.1 | 2.7% | 3.0% |

Example 4

Conjugation of S. Pneumoniae Serotype 23B Polysaccharides to CRM197 Using Reductive Amination in Dimethylsulfoxide Polysaccharide was dissolved, sized to a target molecular mass, chemically activated and buffer-exchanged by ultrafiltration. Activated polysaccharide and purified CRM197 were individually lyophilized and redissolved in dimethyl sulfoxide (DMSO). Redissolved polysaccharide and CRM197 solutions were then combined and conjugated as described below. The resulting conjugate was purified by ultrafiltration prior to a final 0.2-micron filtration. Several process parameters within each step, such as pH, temperature, concentration, and time were controlled to yield conjugates with desired attributes.

Polysaccharide Size Reduction and Oxidation

Purified pneumococcal capsular Ps powder was dissolved in water and 0.45-micron filtered. Dissolved polysaccharide was homogenized to reduce the molecular mass of the Ps. Homogenization pressure and number of passes through the homogenizer were controlled to 400 bar/5 passes.

Size-reduced polysaccharide was concentrated and diafiltered against water using a 10 kDa NMWCO tangential flow ultrafiltration membrane.

The polysaccharide solution was then adjusted to 22° C. and pH 5 with a sodium acetate buffer to minimize polysaccharide size reduction due to activation. Polysaccharide activation was initiated with the addition of a 100 mM sodium metaperiodate solution. Sodium metaperiodate added at 0.10-0.13 moles of sodium metaperiodate per mole of polysaccharide repeating unit to achieve a target level of polysaccharide activation (moles aldehyde per mole of polysaccharide repeating unit).

The activated product was diafiltered against 10 mM potassium phosphate, pH 6.4 followed by diafiltration against water using a 10 kDa NMWCO tangential flow ultrafiltration membrane. Ultrafiltration was conducted at 2-8° C.

Polysaccharide Conjugation to CRM197

Purified CRM197, obtained through expression in Pseudomonas fluorescens as previously described (WO 2012/173876 A1), was diafiltered against 2 mM phosphate, pH 7.0 buffer using a 5 kDa NMWCO tangential flow ultrafiltration membrane and 0.2-micron filtered.

Activated polysaccharides were formulated for lyophilization at 6 mg Ps/mL with sucrose concentration of 5% w/v. CRM197 was formulated for lyophilization at 6 mg Pr/mL with sucrose concentration of 1% w/v.

Formulated Ps and CRM197 solutions were individually lyophilized. Lyophilized Ps and CRM197 materials were redissolved individually in equal volumes of DMSO. The polysaccharide solution was spiked with sodium chloride to a final concentration of 0-50 mM. The polysaccharide and CRM197 solutions were blended to achieve a polysaccharide concentration of 5.0 g Ps/L and a polysaccharide to CRM197 mass ratio of 1.5. The mass ratio was selected to control the polysaccharide to CRM197 ratio in the resulting conjugate. Sodium cyanoborohydride (1 mole per mole of polysaccharide repeating unit) was added, and conjugation proceeded for 2-4 hours at 22° C.

Reduction with Sodium Borohydride

Sodium borohydride (2 mole per mole of polysaccharide repeating unit) was added following the conjugation reaction and incubated for 1 hour at 22° C. The batch was diluted into 150 mM sodium chloride, with approximately 0.025% (w/v) polysorbate 20, at approximately 4° C. Potassium phosphate buffer was then added to neutralize the pH. The batch was concentrated and diafiltered at approximately 4° C. against 150 mM sodium chloride, 25 mM potassium phosphate pH 7, using a 30 kD NMWCO tangential flow ultrafiltration membrane.

Final Filtration and Product Storage

The batch was then concentrated and diafiltered against 10 mM histidine in 150 mM sodium chloride, pH 7.0, with 0.015% (w/v) polysorbate 20, at 4° C. using a 300 kDa NMWCO tangential flow ultrafiltration membrane.

The retentate batch was 0.2 micron filtered then diluted with additional 10 mM histidine in 150 mM sodium chloride, pH 7.0 with 0.015% (w/v) polysorbate 20, dispensed into aliquots and frozen at ≤−60° C.

Table 2 shows the attributes of S. pneumoniae serotype 23B polysaccharide conjugate prepared in DMSO.

TABLE 2

Attributes of S. pneumoniae serotype 23B polysaccharide conjugate from DMSO conjugation

| Oxidized Ps Mw | Conjugate Mw | Ps:Pr | Lysine Consumption (mol/mol CRM197) | Free Ps/ Total Ps | Free Protein/ Total Protein |
|---|---|---|---|---|---|
| 179 kD | 3299 kD | 1.28 | 6.2 | 13% | 5.1% |

Example 5

Formulation of Monovalent Conjugates

Pneumococcal polysaccharide-CRM197 conjugates from serotypes 23A and 23B were prepared as described in Examples 3 and 4. Pneumococcal polysaccharide-CRM197 conjugates from serotype 23F were prepared as described in U.S. Pat. No. 8,192,746. The required volume of bulk conjugates needed to obtain the target concentration of individual serotypes were calculated based on batch volume and concentration of individual bulk polysaccharide concentrations. Bulk conjugates of the S. pneumoniae serotypes (23A, 23B, and 23F) were combined with excipients, sterile filtered and added to APA under mixing conditions. The final concentration of each monovalent conjugate vaccine was 4 µg/mL (w/v PnPs) with 20 mM Histidine, 150 mM NaCl, 0.2% (w/v) PS-20 and 0.250 mg/mL (w/v Al) in the form of APA.

Example 6

Monovalent Conjugate New Zealand White Rabbit Immunogenicity Study

The immunogenicity of the monovalent conjugates was evaluated in a New Zealand White Rabbit (NZWR) model.

Adult New Zealand White rabbits (NZWR, n=3/group) were intramuscularly (IM) immunized with 0.25 ml of respective monovalent conjugate vaccine on day 0 and day 14 (alternating sides). Monovalent pneumococcal conjugate vaccine was dosed at 1 µg PnPs (*S. pneumoniae* serotype 23A or 23B polysaccharide each conjugated to CRM197) with 62.5 µg aluminum phosphate adjuvant (APA) per immunization. Sera were collected prior to study start (pre-immune) and on days 14 (post-dose 1, PD1) and 28 (post-dose 2, PD2). NZWRs were observed at least daily by trained animal care staff for any signs of illness or distress. The vaccine formulations in NZWRs were deemed to be safe and well tolerated. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc (Kenilworth, N.J.) and Covance (Denver, Pa.).

NZWR sera were tested in ELISA assays to evaluate IgG immunogenicity using a 1-2 mg/ml respective PnPs coating concentration. Functional antibody was determined through opsonophagocytosis assays (OPA) based on previously described protocols. See, e.g., Caro-Aguilar et al., 2017, Vaccine 35:865-72 and Burton et al., 2006, Clin Vaccine Immunol 13(9):1004-9.

Figure 9:
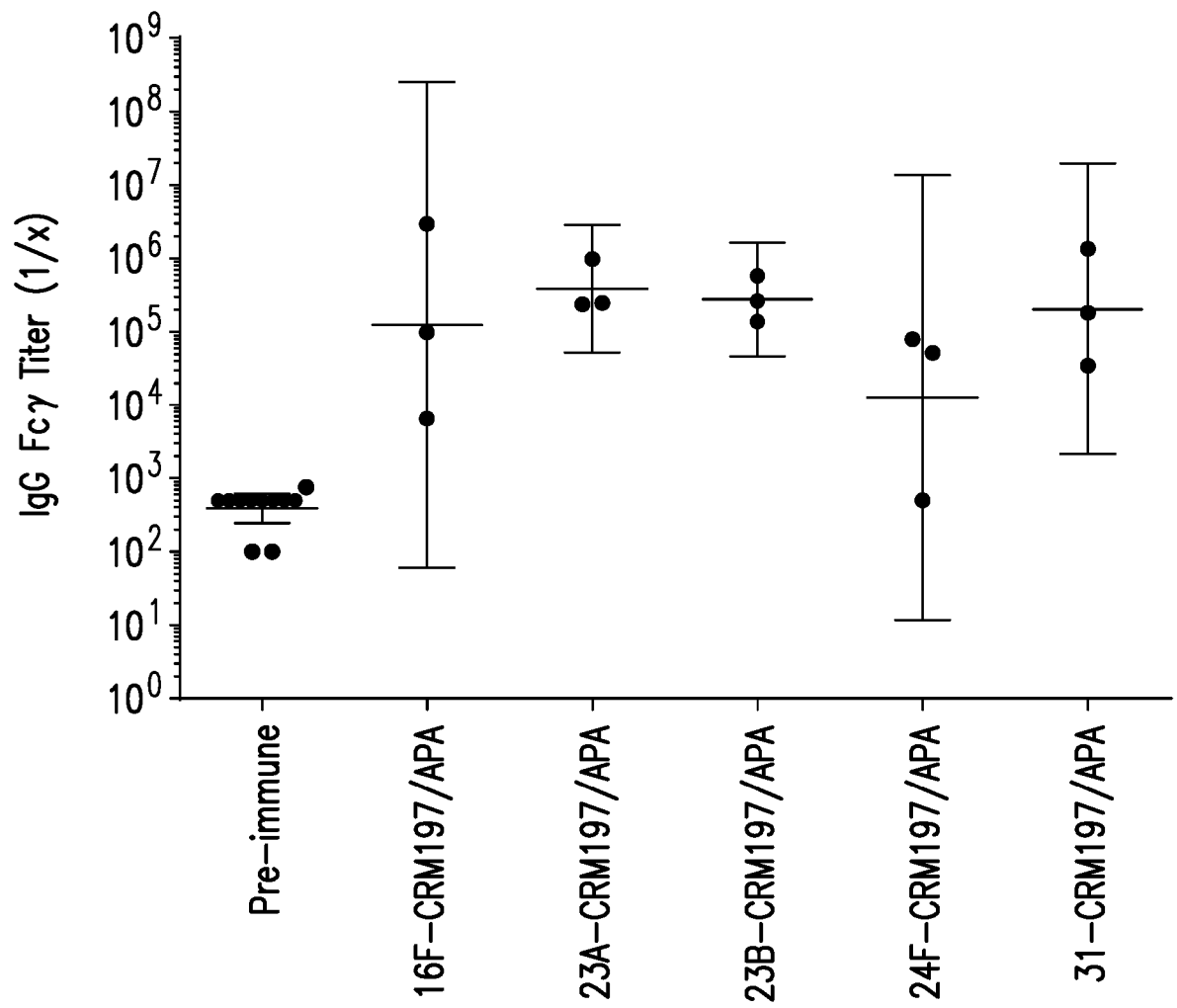
FIG. 9: ELISA IgG antibody titers (post-dose 2) for rabbits immunized with *S. pneumoniae* monovalent polysaccharide serotypes conjugated to CRM197 and formulated with aluminum phosphate adjuvant (APA). Error bars represent the geometric mean+95% confidence interval.
Figure 10:
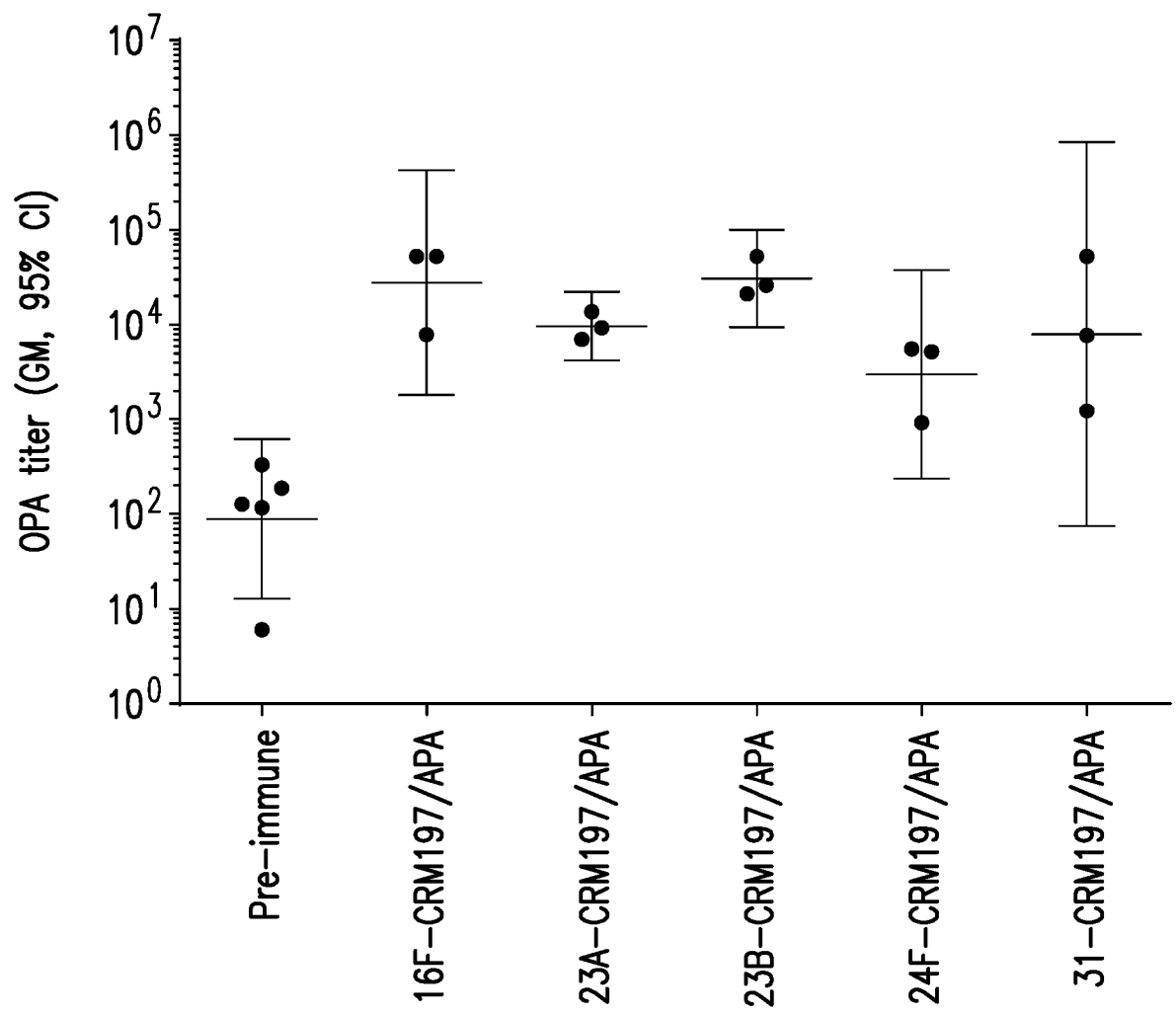
FIG. 10: Serotype specific OPA titers (post-dose 2) for rabbits immunized with *S. pneumoniae* monovalent polysaccharide serotypes conjugated to CRM197 and formulated with aluminum phosphate adjuvant (APA). Error bars represent the geometric mean+95% confidence interval.
Figure 11A:
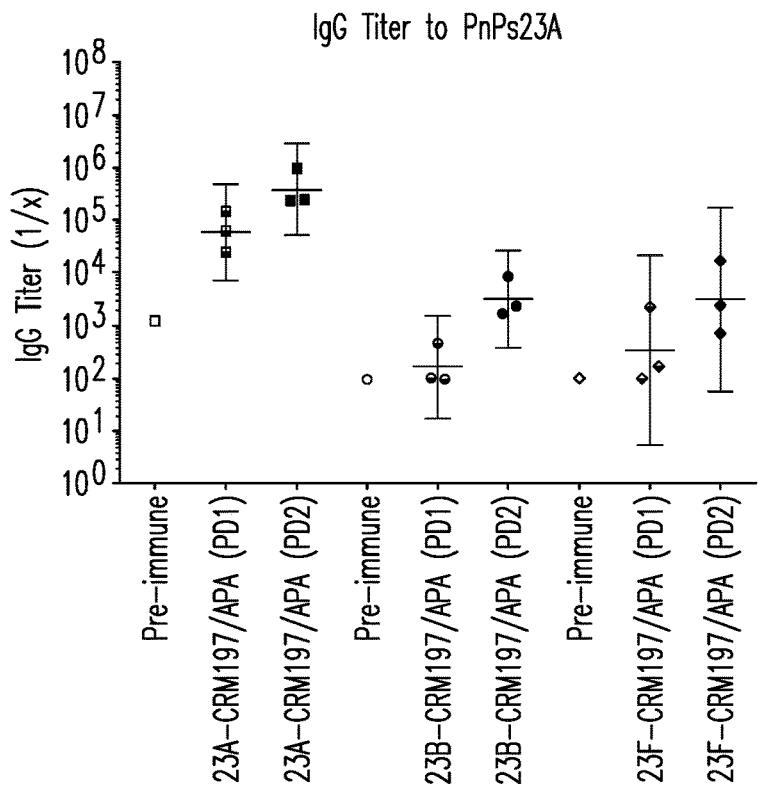
FIGS. 11A-B: A. ELISA PnPs23A IgG antibody titers; and B. *S. pneumoniae* polysaccharide serotype 23A OPA titers (pre-immune, post-dose 1 (PD1) and post-dose 2 (PD2)) for rabbits immunized with *S. pneumoniae* monovalent polysaccharide serotypes 23A, 23B or 23F conjugated to CRM197 and formulated with aluminum phosphate adjuvant (APA). Error bars represent the geometric mean+95% confidence interval.
Figure 11B:
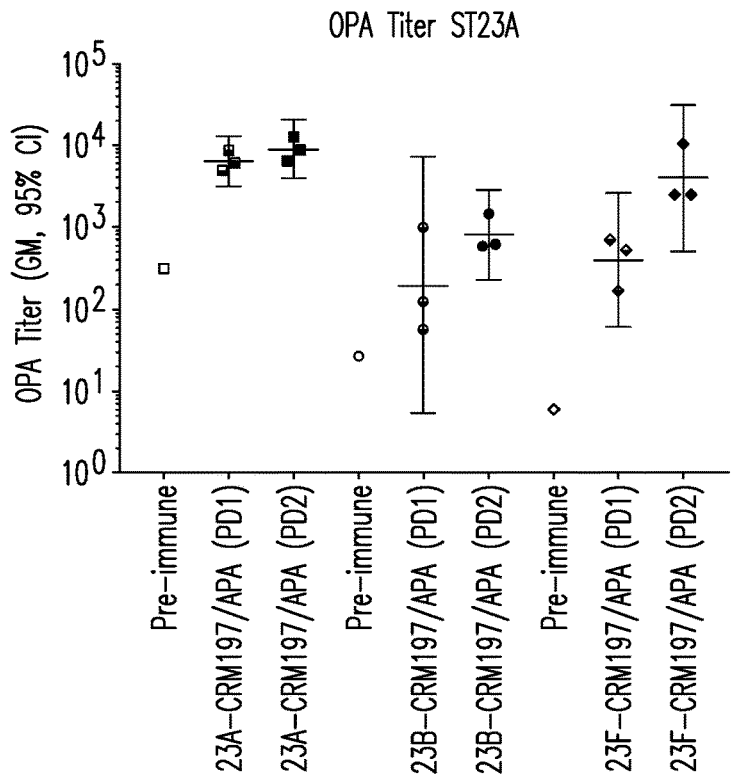

Monovalent pneumococcal polysaccharide conjugate vaccines from *S. pneumoniae* serotypes 23A and 23B were found to be immunogenic in rabbits (FIG. 9) and generate functional antibody which killed the respective bacterial strain (FIG. 10).

Example 7

Monovalent Conjugate New Zealand White Rabbit Immunogenicity Study (23A, 23B, 23F Cross Protection)

Rabbits were immunized with 23A-CRM197/APA, 23B-CRM197/APA or 23F-CRM197/APA to evaluate cross-reactivity between each *S. pneumoniae* serotype.

Figure 12A:
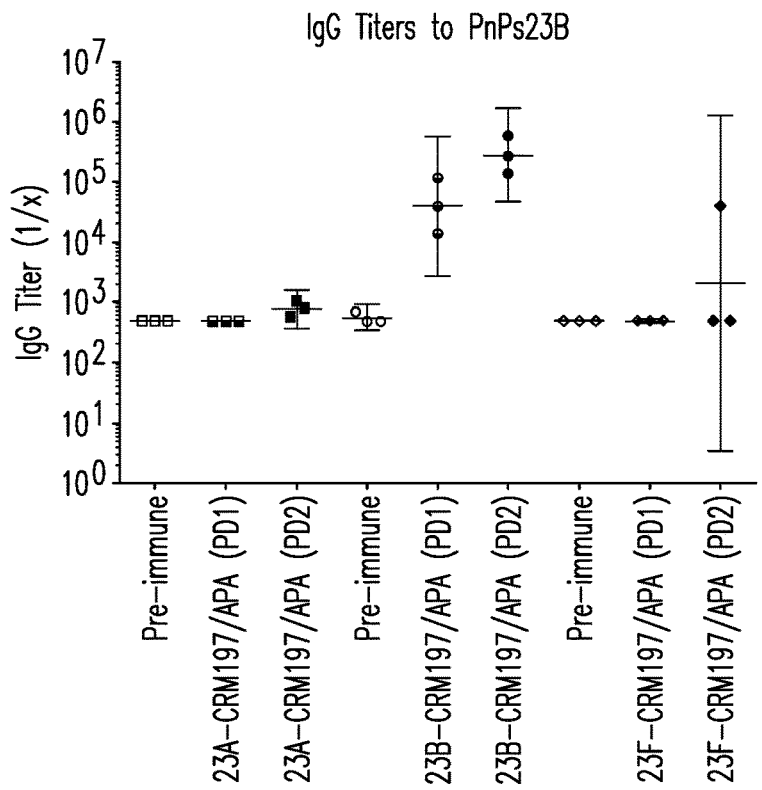
FIGS. 12A-B: A. ELISA PnPs23B IgG antibody titers; and B. *S. pneumoniae* polysaccharide serotype 23B OPA titers (pre-immune, post-dose 1 (PD1) and post-dose 2 (PD2)) for rabbits immunized with *S. pneumoniae* monovalent polysaccharide serotypes 23A, 23B or 23F conjugated to CRM197 and formulated with aluminum phosphate adjuvant (APA). Error bars represent the geometric mean+95% confidence interval.
Figure 12B:
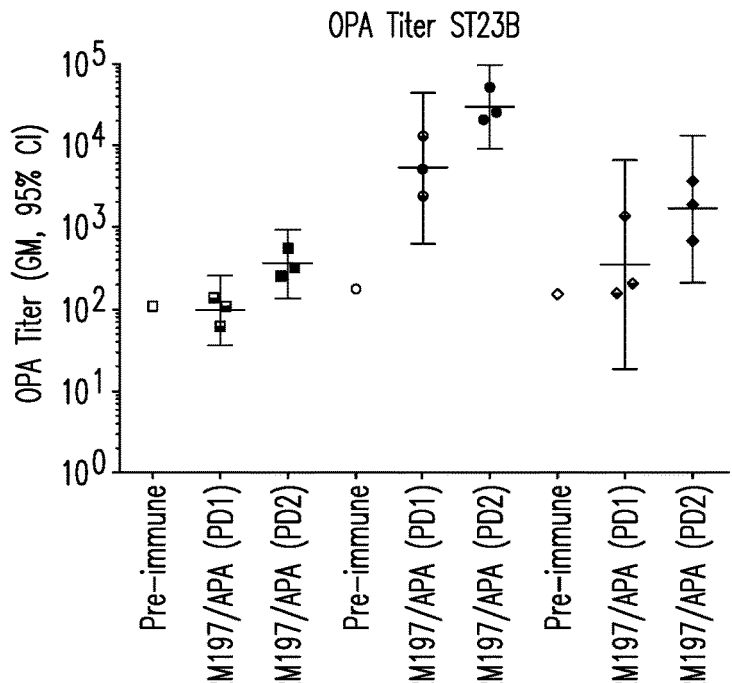
Figure 13A:
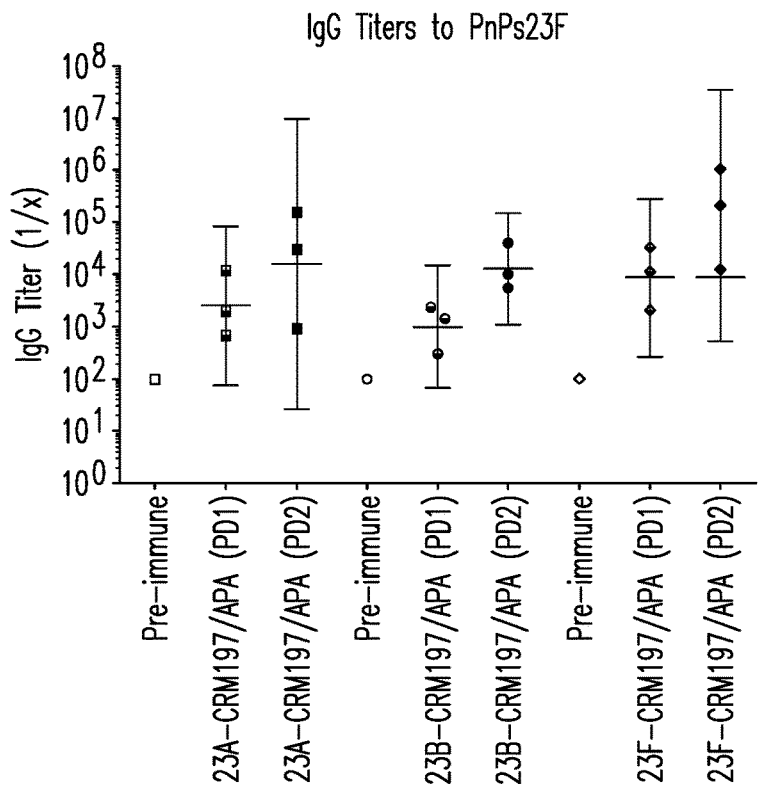
FIGS. 13A-B: A. ELISA PnPs 23F IgG antibody titers; and B. *S. pneumoniae* polysaccharide serotype 23F OPA titers (pre-immune, post-dose 1 (PD1) and post-dose 2 (PD2)) for rabbits immunized with *S. pneumoniae* monovalent polysaccharide serotypes 23A, 23B or 23F conjugated to CRM197 and formulated with aluminum phosphate adjuvant (APA). Error bars represent the geometric mean+95% confidence interval.
Figure 13B:
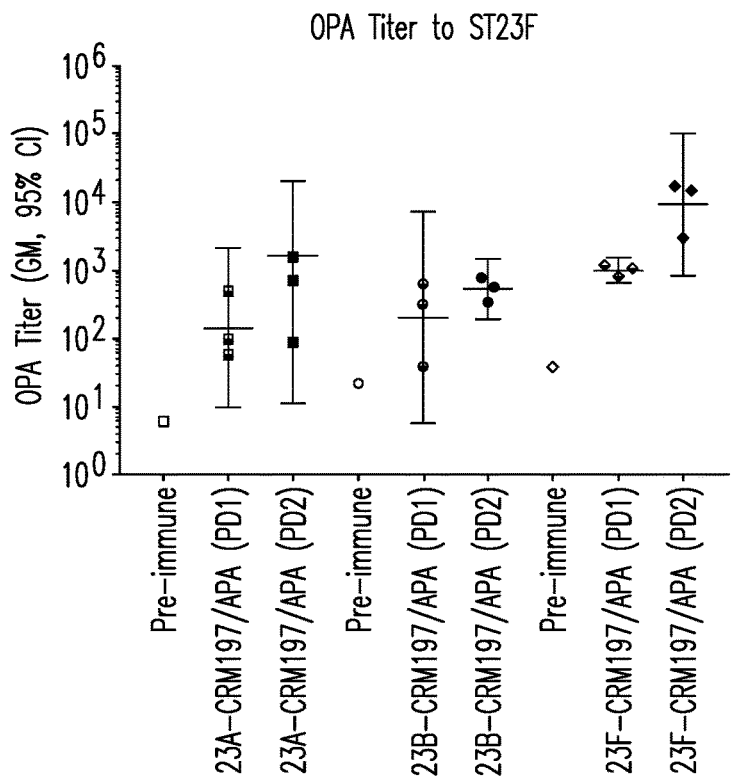

Overall, rabbits immunized with *S. pneumoniae* serogroup 23 monovalent conjugate vaccines had the highest IgG and OPA titers to the homologous polysaccharide and bacterial strain, respectively (FIGS. 11A-B, 12A-B, 13A-B). 23A-CRM197/APA and 23F-CRM197/APA showed low/no cross-reactivity to *S. pneumoniae* 23B serogroup PnPs and bacterial strain compared to rabbits immunized with the 23B-CRM197/APA conjugate (FIGS. 12A-B). Using Dunnett's multiple comparison tests, 23B-CRM197/APA immunized rabbits had significantly higher IgG immunogenicity compared to 23A-CRM197/APA and 23F-CRM197/APA immunized rabbits (P=0.007 and 0.016, respectively) (FIG. 12A). Likewise, 23B-CRM197/APA immunized rabbits had significantly higher functional antibody compared to 23A-CRM197/APA and 23F-CRM197/APA immunized rabbits (P=0.0002 and 0.002, respectively) (FIG. 12B). To cover *S. pneumoniae* serogroup 23, a pneumococcal polysaccharide conjugate vaccine should comprise at least serotype 23A/23F polysaccharides and serotype 23B polysaccharide to protect against *S. pneumoniae* serotypes 23A, 23B, and 23F.

Example 8

Formulation of Pneumococcal Conjugate Vaccines for Rabbit Polyvalent Study

A multivalent pneumococcal conjugate vaccine consisting of different conjugate bulk blend preparations (including from *S. pneumoniae* serotypes 16F, 23A, 23B, 24F and 31) was prepared using pneumococcal polysaccharide-CRM197 conjugates and was formulated in 20 mM histidine pH 5.8 and 150 mM sodium chloride and 0.1% w/v polysorbate-20 (PS-20) at 4 µg/mL each serotype for a total polysaccharide concentration of 84 µg/mL. The conjugates were prepared by individually conjugating the CRM197 protein to pneumococcal polysaccharide (PnPs) types (including from *S. pneumoniae* serotypes 16F, 23A, 23B, 24F and 31). The required volume of bulk conjugates needed to obtain the target concentration of individual serotypes was calculated based on batch volume and concentration of individual bulk polysaccharide concentrations. The individual conjugates were added to a solution of histidine, sodium chloride and Polysorbate-20 (PS-20) to create the conjugate blend. The formulation vessel containing the conjugate blend was mixed using a magnetic stir bar, and sterile filtered into another vessel. The formulations were then filled into plastic syringes, glass syringes, or vials and stored at 2-8° C.

Example 9

Immunogenicity of a Multivalent Pneumococcal Conjugate Vaccine in New Zealand White Rabbits Adult New Zealand White rabbits (NZWR, n=5/group) were intramuscularly (IM) immunized with 0.5 ml of the multivalent pneumococcal conjugate vaccine described in Example 8 on day 0 and day 14 (alternating sides). The multivalent pneumococcal conjugate vaccine was dosed at 2 µg of each conjugated PnPs per immunization. Sera were collected prior to study start (pre-immune) and on days 14 (post-dose 1, PD1) and 28 (post-dose 2, PD2). NZWRs were observed at least daily by trained animal care staff for any signs of illness or distress. The vaccine formulations in NZWRs were deemed to be safe and well tolerated. All animal experiments were performed in strict accordance with the recommendations in the Guide for Care and Use of Laboratory Animals of the National Institutes of Health. The NZWR experimental protocol was approved by the Institutional Animal Care and Use Committees at both Merck & Co., Inc and Covance (Denver, Pa.).

NZWR sera were evaluated for IgG immunogenicity using a multiplexed electrochemiluminescence (ECL) assay. This assay was developed for use with rabbit serum based on the human assay described by Marchese et al. (Optimization and validation of a multiplex, electrochemiluminescence-based detection assay for the quantitation of immunoglobulin G serotype-specific antipneumococcal antibodies in human serum. *Clin Vaccine Immunol.* 16(3): 387-96 (2009)) using technology developed by MesoScale Discovery (a division of MesoScale Diagnostics, LLC, Gaithersburg, Md.) which utilizes a SULFO-TAG™ label that emits light upon electrochemical stimulation. SULFO-TAG™-labeled anti-rabbit IgG was used as the secondary antibody for testing NZWR serum samples. Functional antibody was determined through multiplexed opsonophagocytic assays (MOPA) based on previously described protocols available online at the Bacterial Respiratory Pathogen Reference Laboratory at the University of Alabama at Birmingham using Opsotiter® 3 software (UAB Research Foundation, Caro-Aguilar et al, 2017, supra, Burton et al., 2006, supra).

Figure 14:
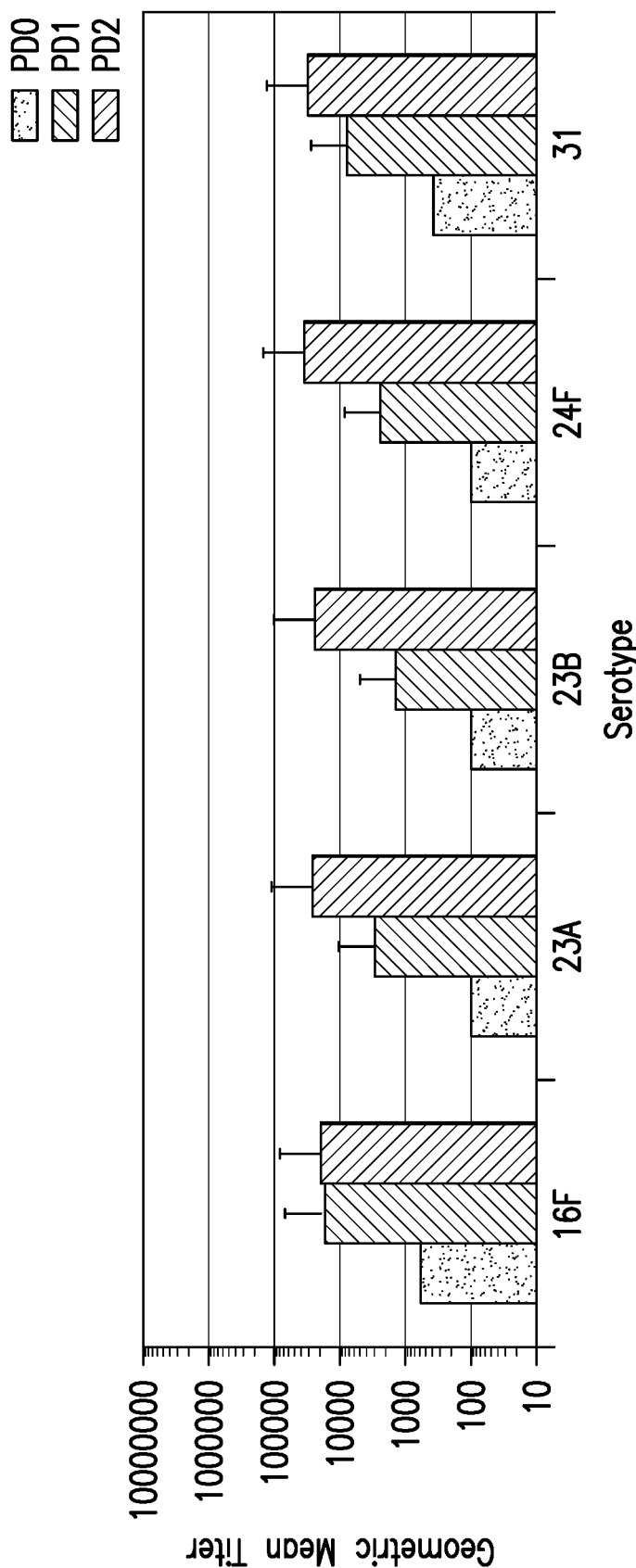
FIG. 14 shows serotype specific (*S. pneumoniae* serotypes 16F, 23A, 23B, 24F, 31) pre-immune, PD1 and PD2 geometric mean antibody titers for rabbits immunized with a multivalent pneumococcal conjugate vaccine (2 μg/PnPs). Error bars represent 2 standard errors of the geometric mean titer of each serotype (X-axis).
Figure 15:
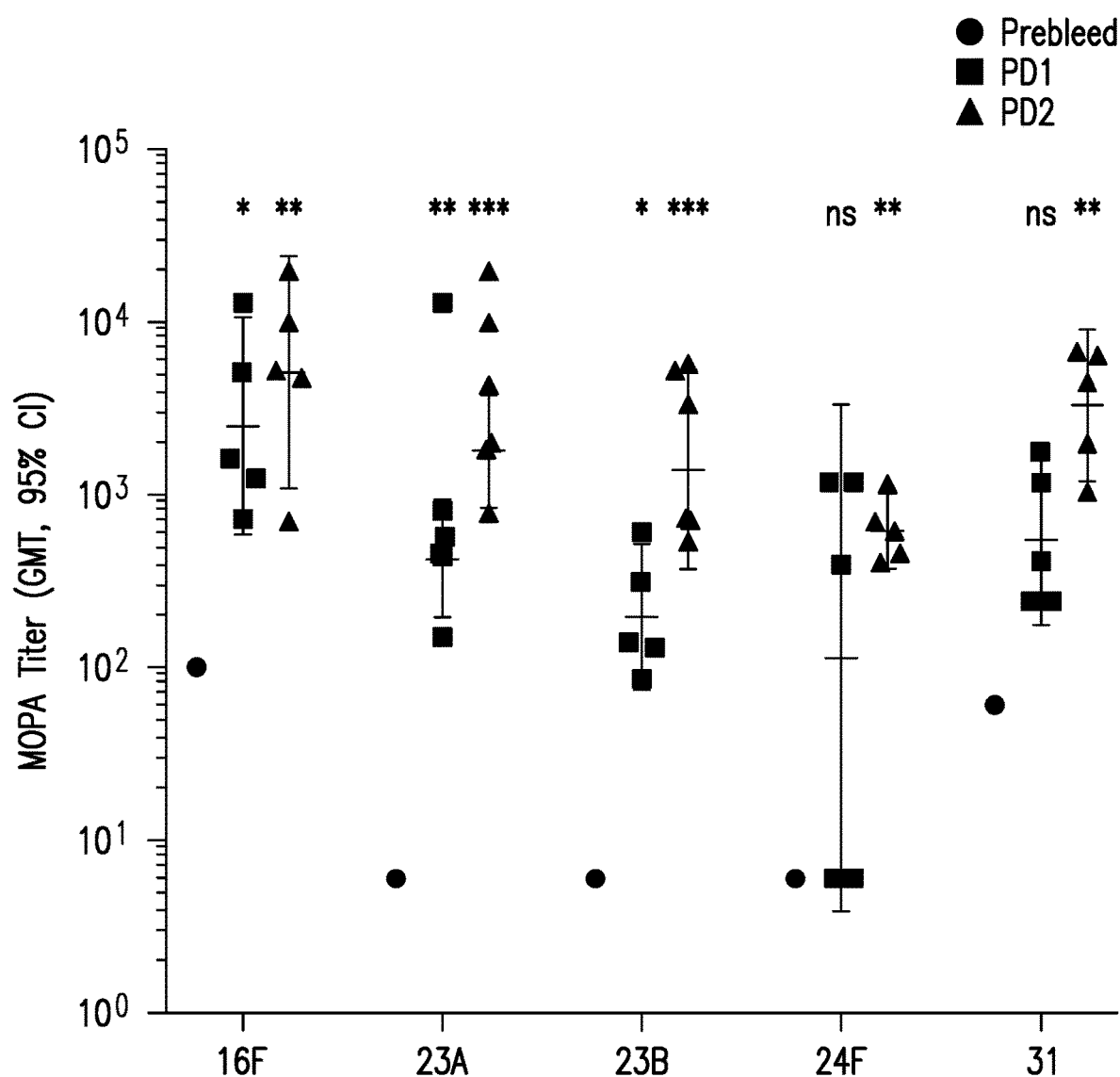
FIG. 15 shows serotype specific (*S. pneumoniae* serotypes 16F, 23A, 23B, 24F, 31) pre-immune, PD1 and PD2 OPA dilution titers for rabbits immunized with a multivalent pneumococcal conjugate vaccine (2 μg/PnPs). Symbols indicate the individual titers and error bars represent the 95% confidence intervals (CIs) of the geometric mean titers (GMTs). $*p<0.05$, $p<0.01$, $*p<0.001$, ns=not significant.

Polysaccharide-protein conjugates prepared from *S. pneumoniae* serotypes 16F, 23A, 23B, 24F, and 31 in a multivalent pneumococcal conjugate vaccine were found to be immunogenic for both post dose 1 (PD1) and post dose 2 (PD2) in rabbits (FIG. 14). They also generated functional antibody which killed vaccine-type bacterial strains (FIG. 15). Rabbits immunized with the multivalent pneumococcal conjugate vaccine at the 2 µg dose had significantly higher PD1 MOPA titers for four serotypes compared to pre-immune rabbit sera (FIG. 15). Rabbits immunized with the multivalent pneumococcal conjugate vaccine at the 2 µg dose had significantly higher PD2 MOPA titers for all five serotypes compared to pre-immune rabbit sera (FIG. 15). Log Transformed data were analyzed by One-way ANOVA with Dunnett's test to determine significance.

What is claimed is:

1. A polysaccharide-carrier protein conjugate, wherein the polysaccharide has an *S. pneumoniae* serotype 23B polysaccharide repeating unit of the following structure:

$$[\rightarrow 4)\text{-}\beta\text{-}Glcp(1\rightarrow 4)\text{-}\beta\text{-}Galp(1\rightarrow 4)\text{-}\beta\text{-}Rhap(1\rightarrow]$$
$$\underset{\uparrow}{3}$$
$$\text{glycerol-2-PO}_4$$

wherein the carrier protein is CRM197, and further wherein the conjugate has a molecular weight from 1,000 kDa to 10,000 kDa.

2. The polysaccharide-carrier protein conjugate of claim 1, wherein the polysaccharide-carrier protein conjugate has a polysaccharide to carrier protein mass ratio from 0.4 to 2.0.

3. The polysaccharide-carrier protein conjugate of claim 1, wherein the carrier protein is conjugated to the serotype 23B polysaccharide unit through the $2^{nd}$ or $3^{rd}$ carbon of the rhamnose sugar.

4. The polysaccharide-carrier protein conjugate of claim 1, wherein the polysaccharide has a molecular weight of between 50 kDa and 1,000 kDa.

5. The polysaccharide-carrier protein conjugate of claim 1, wherein the polysaccharide has a molecular weight of between 100 kDa and 800 kDa.

6. The polysaccharide-carrier protein conjugate of claim 1, wherein the polysaccharide has a molecular weight of between 100 kDa and 300 kDa.

7. The polysaccharide-carrier protein conjugate of claim 1, wherein the degree of conjugation of the conjugate is between 2 and 15.

8. The polysaccharide-carrier protein conjugate of claim 1, wherein the degree of conjugation of the conjugate is between 8 and 12.

9. The polysaccharide-carrier protein conjugate of claim 1, wherein the polysaccharide-carrier protein conjugate has a polysaccharide to carrier protein mass ratio from 0.5 to 3.0.

10. The polysaccharide-carrier protein conjugate of claim 1, wherein the polysaccharide-carrier protein conjugate has a polysaccharide to carrier protein mass ratio from 0.5 to 1.5.

11. The polysaccharide-carrier protein conjugate of claim 1, wherein the polysaccharide-carrier protein conjugate has a polysaccharide to carrier protein mass ratio of about 1.3.

12. The polysaccharide-carrier protein conjugate of claim 1, wherein the polysaccharide-carrier protein conjugate comprises less than about 30% of non-covalently associated polysaccharide compared to the total amount of polysaccharide.

13. The polysaccharide-carrier protein conjugate of claim 1, wherein the polysaccharide-carrier protein conjugate comprises less than about 25% of non-covalently associated polysaccharide compared to the total amount of polysaccharide.

14. The polysaccharide-carrier protein conjugate of claim 1, wherein the polysaccharide-carrier protein conjugate comprises less than about 20% of non-covalently associated polysaccharide compared to the total amount of polysaccharide.

15. The polysaccharide-carrier protein conjugate of claim 1, wherein the polysaccharide-carrier protein conjugate comprises less than about 15% of non-covalently associated polysaccharide compared to the total amount of polysaccharide.

16. The polysaccharide-carrier protein conjugate of claim 1, wherein the polysaccharide has a molecular weight of between 100 kDa and 300 kDa; wherein the degree of conjugation of the conjugate is between 4 and 7; wherein the mass ratio of polysaccharide to carrier protein in the conjugate is between 0.5 and 1.5; and wherein the conjugate comprises less than about 15% of free polysaccharide compared to the total amount of polysaccharide.

17. A polysaccharide-carrier protein conjugate, wherein the polysaccharide has an *S. pneumoniae* serotype 23B polysaccharide repeating unit of the following structure:

$$[\rightarrow 4)\text{-}\beta\text{-}Glcp(1\rightarrow 4)\text{-}\beta\text{-}Galp(1\rightarrow 4)\text{-}\beta\text{-}Rhap(1\rightarrow]$$
$$\underset{\uparrow}{3}$$
$$\text{glycerol-2-PO}_4$$

wherein the carrier protein is CRM197; and further wherein the wherein the polysaccharide-carrier protein conjugate has a polysaccharide to carrier protein mass ratio from 0.5 to 3.0.

18. The polysaccharide-carrier protein conjugate of claim 17, wherein the polysaccharide-carrier protein conjugate has a polysaccharide to carrier protein mass ratio from 0.5 to 1.5.

19. The polysaccharide-carrier protein conjugate of claim 17, wherein the polysaccharide-carrier protein conjugate has a polysaccharide to carrier protein mass ratio of about 1.3.

20. The polysaccharide-carrier protein conjugate of claim 17, wherein the carrier protein is conjugated to the serotype 23B polysaccharide unit through the $2^{nd}$ or $3^{rd}$ carbon of the rhamnose sugar.

21. The polysaccharide-carrier protein conjugate of claim 17, wherein the polysaccharide has a molecular weight of between 50 kDa and 1,000 kDa.

22. The polysaccharide-carrier protein conjugate of claim 17, wherein the polysaccharide has a molecular weight of between 100 kDa and 800 kDa.

23. The polysaccharide-carrier protein conjugate of claim 17, wherein the polysaccharide has a molecular weight of between 100 kDa and 300 kDa.

24. The polysaccharide-carrier protein conjugate of claim 17, wherein the degree of conjugation of the conjugate is between 2 and 15.

25. The polysaccharide-carrier protein conjugate of claim 17, wherein the degree of conjugation of the conjugate is between 8 and 12.

26. The polysaccharide-carrier protein conjugate of claim 17, wherein the polysaccharide-carrier protein conjugate comprises less than about 30% of non-covalently associated polysaccharide compared to the total amount of polysaccharide.

27. The polysaccharide-carrier protein conjugate of claim 17, wherein the polysaccharide-carrier protein conjugate comprises less than about 25% of non-covalently associated polysaccharide compared to the total amount of polysaccharide.

28. The polysaccharide-carrier protein conjugate of claim 17, wherein the polysaccharide-carrier protein conjugate comprises less than about 20% of non-covalently associated polysaccharide compared to the total amount of polysaccharide.

29. The polysaccharide-carrier protein conjugate of claim 17, wherein the polysaccharide-carrier protein conjugate comprises less than about 15% of non-covalently associated polysaccharide compared to the total amount of polysaccharide.

30. The polysaccharide-carrier protein conjugate of claim 17, wherein the polysaccharide has a molecular weight of between 100 kDa and 300 kDa; wherein the degree of conjugation of the conjugate is between 4 and 7; wherein the mass ratio of polysaccharide to carrier protein in the conjugate is between 0.5 and 1.5; wherein the conjugate comprises less than about 15% of free polysaccharide compared to the total amount of polysaccharide; and wherein the conjugate has a molecular weight from 1,000 kDa to 10,000 kDa.

* * * * *